US009301831B2

(12) United States Patent
Kusleika et al.

(10) Patent No.: US 9,301,831 B2
(45) Date of Patent: Apr. 5, 2016

(54) METHODS FOR ATTAINING A PREDETERMINED POROSITY OF A VASCULAR DEVICE

(71) Applicant: COVIDIEN LP, Mansfield, MA (US)

(72) Inventors: Rich Kusleika, Eden Prairie, MN (US); Mike Louis Losordo, San Juan Capistrano, CA (US)

(73) Assignee: Covidien LP, Mansfield, MA (US)

( * ) Notice: Subject to any disclaimer, the term of this patent is extended or adjusted under 35 U.S.C. 154(b) by 195 days.

(21) Appl. No.: 13/827,030

(22) Filed: Mar. 14, 2013

(65) Prior Publication Data
US 2014/0121746 A1    May 1, 2014

Related U.S. Application Data

(60) Provisional application No. 61/720,154, filed on Oct. 30, 2012.

(51) Int. Cl.
*A61F 2/06* (2013.01)
*A61F 2/07* (2013.01)
*A61F 2/90* (2013.01)
*A61F 2/958* (2013.01)
*A61F 2/82* (2013.01)

(52) U.S. Cl.
CPC ... *A61F 2/07* (2013.01); *A61F 2/90* (2013.01); *A61F 2/958* (2013.01); *A61F 2002/823* (2013.01); *A61F 2220/005* (2013.01); *A61F 2220/0008* (2013.01); *A61F 2250/0007* (2013.01); *A61F 2250/0012* (2013.01); *A61F 2250/0018* (2013.01); *A61F 2250/0023* (2013.01); *A61F 2250/0029* (2013.01); *A61F 2250/0039* (2013.01); *A61F 2250/0048* (2013.01)

(58) Field of Classification Search
None
See application file for complete search history.

(56) References Cited

U.S. PATENT DOCUMENTS

| 2,919,467 | A | 1/1960 | Mercer |
| 4,321,711 | A | 3/1982 | Mano |
| 4,503,569 | A | 3/1985 | Dotter |
| 4,512,338 | A | 4/1985 | Balko et al. |

(Continued)

FOREIGN PATENT DOCUMENTS

| CN | 101472537 A | 7/2009 |
| EP | 855170 | 7/1998 |

(Continued)

OTHER PUBLICATIONS

Benndorf, et al. Treatment of a Ruptured Dissecting Vertebral Artery Aneurysm with Double Stent Placement: Case Report AJNR Am J Neuroradiol, Nov.-Dec. 2001, vol. 22, pp. 1844-1848.

(Continued)

*Primary Examiner* — Tuan V Nguyen
(74) *Attorney, Agent, or Firm* — Mark J. Kertz, Esq.

(57) ABSTRACT

A method for manufacturing a vascular device that includes disposing a vascular device over an expanding member. The device includes a body having a substantially uniform porosity that is adapted to change by adjusting an axial length of the body. The method also includes adhering a portion of the body to the expanding member such that upon radial expansion of the expanding member, adherence between the body portion and the expanding member reduces a porosity of the body within the body portion more than the body porosity is reduced outside the portion.

26 Claims, 11 Drawing Sheets

(56) References Cited

U.S. PATENT DOCUMENTS

| | | |
|---|---|---|
| 4,538,622 A | 9/1985 | Samson et al. |
| 4,572,186 A | 2/1986 | Gould et al. |
| 4,580,568 A | 4/1986 | Gianturco |
| 4,655,771 A | 4/1987 | Wallsten |
| 4,681,110 A | 7/1987 | Wiktor |
| 4,733,665 A | 3/1988 | Palmaz |
| 4,743,251 A | 5/1988 | Barra |
| 4,768,507 A | 9/1988 | Fischell et al. |
| 4,776,337 A | 10/1988 | Palmaz |
| 4,856,516 A | 8/1989 | Hillstead |
| 4,954,126 A | 9/1990 | Wallsten |
| 5,011,488 A | 4/1991 | Ginsburg |
| 5,035,706 A | 7/1991 | Giantureo et al. |
| 5,041,126 A | 8/1991 | Gianturco |
| 5,061,275 A | 10/1991 | Wallsten et al. |
| 5,108,416 A | 4/1992 | Ryan et al. |
| 5,160,341 A | 11/1992 | Brenneman et al. |
| 5,180,368 A | 1/1993 | Garrison |
| 5,192,297 A | 3/1993 | Hull |
| 5,197,978 A | 3/1993 | Hess |
| 5,201,757 A | 4/1993 | Heyn et al. |
| 5,209,731 A | 5/1993 | Sterman et al. |
| 5,242,399 A | 9/1993 | Lau et al. |
| 5,246,420 A | 9/1993 | Kraus et al. |
| 5,246,445 A | 9/1993 | Yachia et al. |
| 5,344,426 A | 9/1994 | Lau et al. |
| 5,360,443 A | 11/1994 | Barone et al. |
| 5,382,259 A | 1/1995 | Phelps et al. |
| 5,401,257 A | 3/1995 | Chevalier, Jr. et al. |
| 5,405,377 A | 4/1995 | Cragg |
| 5,405,380 A | 4/1995 | Gianotti et al. |
| 5,415,637 A | 5/1995 | Khosravi |
| 5,421,826 A | 6/1995 | Crocker et al. |
| 5,423,849 A | 6/1995 | Engelson et al. |
| 5,449,372 A | 9/1995 | Schmaltz et al. |
| 5,458,615 A | 10/1995 | Klemm et al. |
| 5,476,505 A | 12/1995 | Limon |
| 5,480,423 A | 1/1996 | Ravenscroft et al. |
| 5,484,444 A | 1/1996 | Braunschweiler et al. |
| 5,489,295 A | 2/1996 | Piplani et al. |
| 5,507,768 A | 4/1996 | Lau et al. |
| 5,522,822 A | 6/1996 | Phelps et al. |
| 5,534,007 A | 7/1996 | St. Germain et al. |
| 5,545,208 A | 8/1996 | Wolff et al. |
| 5,546,880 A | 8/1996 | Ronyak et al. |
| 5,549,662 A | 8/1996 | Fordenbacher |
| 5,562,641 A | 10/1996 | Flomenblit et al. |
| 5,562,728 A | 10/1996 | Lazarus et al. |
| 5,591,225 A | 1/1997 | Okuda |
| 5,599,291 A | 2/1997 | Balbierz et al. |
| 5,601,593 A | 2/1997 | Freitag |
| 5,607,466 A | 3/1997 | Imbert et al. |
| 5,609,625 A | 3/1997 | Piplani et al. |
| 5,626,602 A | 5/1997 | Gianotti et al. |
| 5,628,783 A | 5/1997 | Quiachon et al. |
| 5,628,788 A | 5/1997 | Pinchuk |
| 5,632,771 A | 5/1997 | Boatman et al. |
| 5,632,772 A | 5/1997 | Alcime et al. |
| 5,636,641 A | 6/1997 | Fariabi |
| 5,637,113 A | 6/1997 | Tartaglia et al. |
| 5,639,278 A | 6/1997 | Dereume et al. |
| 5,645,559 A | 7/1997 | Hachtman et al. |
| D381,932 S | 8/1997 | Walshe et al. |
| 5,667,522 A | 9/1997 | Flomenblit et al. |
| 5,674,276 A | 10/1997 | Andersen et al. |
| 5,683,451 A | 11/1997 | Lenker et al. |
| 5,690,120 A | 11/1997 | Jacobsen et al. |
| 5,690,644 A | 11/1997 | Yurek et al. |
| 5,695,499 A | 12/1997 | Helgerson et al. |
| 5,700,269 A | 12/1997 | Pinchuk et al. |
| 5,702,418 A | 12/1997 | Ravenscroft |
| 5,709,702 A | 1/1998 | Cogita |
| 5,709,703 A | 1/1998 | Lukic et al. |
| 5,718,159 A | 2/1998 | Thompson |
| 5,725,570 A | 3/1998 | Heath |
| 5,733,327 A | 3/1998 | Igaki et al. |
| 5,735,859 A | 4/1998 | Fischell et al. |
| 5,741,325 A | 4/1998 | Chaikof et al. |
| 5,741,333 A | 4/1998 | Frid |
| 5,746,765 A | 5/1998 | Kleshinski et al. |
| 5,749,883 A | 5/1998 | Halpern |
| 5,749,920 A | 5/1998 | Quiachon et al. |
| 5,769,884 A | 6/1998 | Solovay |
| 5,769,885 A | 6/1998 | Quiachon et al. |
| 5,776,099 A | 7/1998 | Tremulis |
| 5,776,142 A | 7/1998 | Gunderson |
| 5,782,909 A | 7/1998 | Quiachon et al. |
| 5,797,952 A | 8/1998 | Klein |
| 5,800,518 A | 9/1998 | Piplani et al. |
| 5,810,837 A | 9/1998 | Hofmann et al. |
| 5,817,102 A | 10/1998 | Johnson et al. |
| 5,824,039 A | 10/1998 | Piplani et al. |
| 5,824,041 A | 10/1998 | Lenker et al. |
| 5,824,042 A | 10/1998 | Lombardi et al. |
| 5,824,044 A | 10/1998 | Quiachon et al. |
| 5,824,058 A | 10/1998 | Ravenscroft et al. |
| 5,830,229 A | 11/1998 | Konya et al. |
| 5,833,632 A | 11/1998 | Jacobsen et al. |
| 5,836,868 A | 11/1998 | Ressemann et al. |
| 5,843,168 A | 12/1998 | Dang |
| 5,868,754 A | 2/1999 | Levine et al. |
| 5,876,419 A | 3/1999 | Carpenter et al. |
| 5,888,201 A | 3/1999 | Stinson et al. |
| 5,902,266 A | 5/1999 | Leone et al. |
| 5,902,317 A | 5/1999 | Kleshinski et al. |
| 5,906,640 A | 5/1999 | Penn et al. |
| 5,911,717 A | 6/1999 | Jacobsen et al. |
| 5,916,194 A | 6/1999 | Jacobsen et al. |
| 5,919,204 A | 7/1999 | Lukic et al. |
| 5,928,260 A | 7/1999 | Chin et al. |
| 5,944,728 A | 8/1999 | Bates |
| 5,951,599 A | 9/1999 | McCrory |
| 5,957,973 A | 9/1999 | Quiachon et al. |
| 5,957,974 A | 9/1999 | Thompson et al. |
| 5,964,797 A | 10/1999 | Ho |
| 5,980,530 A | 11/1999 | Willard et al. |
| 5,980,533 A | 11/1999 | Holman |
| 6,012,277 A | 1/2000 | Prins et al. |
| 6,014,919 A | 1/2000 | Jacobsen et al. |
| 6,015,432 A | 1/2000 | Rakos et al. |
| 6,017,319 A | 1/2000 | Jacobsen et al. |
| 6,019,778 A | 2/2000 | Wilson et al. |
| 6,019,786 A | 2/2000 | Thompson |
| 6,022,369 A | 2/2000 | Jacobsen et al. |
| 6,024,754 A | 2/2000 | Engelson |
| 6,024,763 A | 2/2000 | Lenker et al. |
| 6,027,516 A | 2/2000 | Kolobow et al. |
| 6,033,436 A | 3/2000 | Steinke et al. |
| 6,039,721 A | 3/2000 | Johnson et al. |
| 6,039,758 A | 3/2000 | Quiachon et al. |
| 6,042,589 A | 3/2000 | Marianne |
| 6,051,021 A | 4/2000 | Frid |
| 6,056,993 A | 5/2000 | Leidner et al. |
| 6,063,111 A | 5/2000 | Hieshima et al. |
| 6,074,407 A | 6/2000 | Levine et al. |
| 6,077,295 A | 6/2000 | Limon et al. |
| 6,080,191 A | 6/2000 | Summers |
| 6,083,257 A | 7/2000 | Taylor et al. |
| 6,093,199 A | 7/2000 | Brown et al. |
| 6,096,052 A | 8/2000 | Callister et al. |
| 6,102,942 A | 8/2000 | Ahari |
| 6,123,712 A | 9/2000 | Di Caprio et al. |
| 6,126,685 A | 10/2000 | Lenker et al. |
| 6,132,459 A | 10/2000 | Piplani et al. |
| 6,139,543 A | 10/2000 | Esch et al. |
| 6,146,415 A | 11/2000 | Fitz |
| 6,149,680 A | 11/2000 | Shelso et al. |
| 6,159,228 A | 12/2000 | Frid et al. |
| 6,161,399 A | 12/2000 | Jayaraman |
| 6,165,194 A | 12/2000 | Denardo |
| 6,165,210 A | 12/2000 | Lau et al. |
| 6,165,213 A | 12/2000 | Goicoechea et al. |
| 6,168,592 B1 | 1/2001 | Kupiecki et al. |
| 6,174,330 B1 | 1/2001 | Stinson |

(56) References Cited

U.S. PATENT DOCUMENTS

| | | | |
|---|---|---|---|
| 6,183,410 | B1 | 2/2001 | Jacobsen et al. |
| 6,183,508 | B1 | 2/2001 | Stinson et al. |
| 6,187,013 | B1 * | 2/2001 | Stoltze et al. .......... 606/108 |
| 6,193,708 | B1 | 2/2001 | Ken et al. |
| 6,197,046 | B1 | 3/2001 | Piplani et al. |
| 6,203,569 | B1 | 3/2001 | Wijay |
| 6,206,868 | B1 | 3/2001 | Parodi |
| 6,210,400 | B1 | 4/2001 | Hebert et al. |
| 6,210,434 | B1 | 4/2001 | Quiachon et al. |
| 6,210,435 | B1 | 4/2001 | Piplani et al. |
| 6,214,038 | B1 | 4/2001 | Piplani et al. |
| 6,214,042 | B1 | 4/2001 | Jacobsen et al. |
| 6,221,102 | B1 | 4/2001 | Baker et al. |
| 6,224,609 | B1 | 5/2001 | Ressemann et al. |
| 6,224,829 | B1 | 5/2001 | Piplani et al. |
| 6,231,598 | B1 | 5/2001 | Berry et al. |
| 6,235,050 | B1 | 5/2001 | Quiachon et al. |
| 6,241,759 | B1 | 6/2001 | Piplani et al. |
| 6,245,087 | B1 | 6/2001 | Addis |
| 6,245,103 | B1 | 6/2001 | Stinson |
| 6,251,132 | B1 | 6/2001 | Ravenscroft et al. |
| 6,258,115 | B1 | 7/2001 | Dubrul |
| 6,260,458 | B1 | 7/2001 | Jacobsen et al. |
| 6,261,305 | B1 | 7/2001 | Marotta et al. |
| 6,261,316 | B1 | 7/2001 | Shaolian et al. |
| 6,264,671 | B1 | 7/2001 | Stack et al. |
| 6,264,689 | B1 | 7/2001 | Colgan et al. |
| 6,270,523 | B1 | 8/2001 | Herweck et al. |
| 6,280,465 | B1 | 8/2001 | Cryer |
| 6,287,331 | B1 | 9/2001 | Heath |
| 6,290,721 | B1 | 9/2001 | Heath |
| 6,299,636 | B1 | 10/2001 | Schmitt et al. |
| 6,302,810 | B2 | 10/2001 | Yokota |
| 6,302,893 | B1 | 10/2001 | Limon et al. |
| 6,309,353 | B1 * | 10/2001 | Cheng et al. .......... 600/437 |
| 6,322,576 | B1 | 11/2001 | Wallace et al. |
| 6,322,586 | B1 | 11/2001 | Monroe et al. |
| 6,322,587 | B1 | 11/2001 | Quiachon et al. |
| 6,325,826 | B1 | 12/2001 | Vardi et al. |
| 6,334,871 | B1 | 1/2002 | Dor et al. |
| 6,336,938 | B1 | 1/2002 | Kavteladze et al. |
| 6,340,367 | B1 | 1/2002 | Stinson et al. |
| 6,340,368 | B1 | 1/2002 | Verbeck |
| 6,342,068 | B1 | 1/2002 | Thompson |
| 6,344,041 | B1 | 2/2002 | Kupiecki et al. |
| 6,348,063 | B1 | 2/2002 | Yassour et al. |
| 6,350,199 | B1 | 2/2002 | Williams et al. |
| 6,350,278 | B1 | 2/2002 | Lenker et al. |
| 6,355,051 | B1 | 3/2002 | Sisskind et al. |
| 6,355,061 | B1 | 3/2002 | Quiachon et al. |
| 6,364,895 | B1 | 4/2002 | Greenhalgh |
| 6,368,344 | B1 | 4/2002 | Fitz |
| 6,368,557 | B1 | 4/2002 | Piplani et al. |
| 6,375,670 | B1 | 4/2002 | Greenhalgh |
| 6,375,676 | B1 | 4/2002 | Cox |
| 6,379,618 | B1 | 4/2002 | Piplani et al. |
| 6,380,457 | B1 | 4/2002 | Yurek et al. |
| 6,389,946 | B1 | 5/2002 | Frid |
| 6,395,017 | B1 | 5/2002 | Dwyer et al. |
| 6,395,021 | B1 | 5/2002 | Hart et al. |
| 6,395,022 | B1 | 5/2002 | Piplani et al. |
| 6,398,802 | B1 | 6/2002 | Yee |
| 6,409,683 | B1 | 6/2002 | Fonseca et al. |
| 6,413,235 | B1 | 7/2002 | Parodi |
| 6,416,519 | B1 | 7/2002 | VanDusseldorp |
| 6,416,536 | B1 | 7/2002 | Yee |
| 6,419,693 | B1 | 7/2002 | Fariabi |
| 6,428,489 | B1 | 8/2002 | Jacobsen et al. |
| 6,440,088 | B1 | 8/2002 | Jacobsen et al. |
| 6,443,971 | B1 | 9/2002 | Boylan et al. |
| 6,443,979 | B1 | 9/2002 | Stalker et al. |
| 6,454,999 | B1 | 9/2002 | Farhangnia et al. |
| 6,468,301 | B1 | 10/2002 | Amplatz et al. |
| 6,477,768 | B1 | 11/2002 | Wildner |
| 6,478,778 | B1 | 11/2002 | Jacobsen et al. |
| 6,482,221 | B1 | 11/2002 | Hebert et al. |
| 6,488,705 | B2 | 12/2002 | Schmitt et al. |
| 6,491,648 | B1 | 12/2002 | Cornish et al. |
| 6,494,895 | B2 | 12/2002 | Addis |
| 6,497,711 | B1 | 12/2002 | Plaia et al. |
| 6,503,450 | B1 | 1/2003 | Afzal et al. |
| 6,514,261 | B1 | 2/2003 | Randall et al. |
| 6,514,285 | B1 | 2/2003 | Pinchasik |
| 6,524,299 | B1 | 2/2003 | Tran et al. |
| 6,527,763 | B2 | 3/2003 | Esch et al. |
| 6,533,811 | B1 | 3/2003 | Ryan et al. |
| 6,540,778 | B1 | 4/2003 | Quiachon et al. |
| 6,547,779 | B2 | 4/2003 | Levine et al. |
| 6,551,352 | B2 | 4/2003 | Clerc et al. |
| 6,572,646 | B1 | 6/2003 | Boylan et al. |
| 6,576,006 | B2 | 6/2003 | Limon et al. |
| 6,582,460 | B1 | 6/2003 | Cryer |
| 6,582,461 | B1 | 6/2003 | Burmeister et al. |
| 6,589,273 | B1 | 7/2003 | McDermott |
| 6,592,616 | B1 | 7/2003 | Stack et al. |
| 6,602,271 | B2 | 8/2003 | Adams et al. |
| 6,602,280 | B2 | 8/2003 | Chobotov |
| 6,605,110 | B2 | 8/2003 | Harrison |
| 6,613,075 | B1 | 9/2003 | Healy et al. |
| 6,613,078 | B1 | 9/2003 | Barone |
| 6,622,604 | B1 | 9/2003 | Chouinard et al. |
| 6,623,518 | B2 | 9/2003 | Thompson et al. |
| 6,635,068 | B1 | 10/2003 | Dubrul et al. |
| 6,638,243 | B2 | 10/2003 | Kupiecki |
| 6,645,240 | B2 | 11/2003 | Yee |
| 6,646,218 | B1 | 11/2003 | Campbell et al. |
| 6,652,508 | B2 | 11/2003 | Griffin et al. |
| 6,652,574 | B1 | 11/2003 | Jayaraman |
| 6,656,212 | B2 | 12/2003 | Ravenscroft et al. |
| 6,656,218 | B1 | 12/2003 | Denardo et al. |
| 6,660,024 | B1 | 12/2003 | Flaherty et al. |
| 6,660,032 | B2 | 12/2003 | Klumb et al. |
| 6,663,666 | B1 | 12/2003 | Quiachon et al. |
| 6,666,881 | B1 | 12/2003 | Richter et al. |
| 6,669,719 | B2 | 12/2003 | Wallace et al. |
| 6,673,089 | B1 | 1/2004 | Yassour et al. |
| 6,673,100 | B2 | 1/2004 | Diaz et al. |
| 6,679,893 | B1 | 1/2004 | Tran |
| 6,682,557 | B1 | 1/2004 | Quiachon et al. |
| 6,685,735 | B1 | 2/2004 | Ahari |
| 6,689,120 | B1 | 2/2004 | Gerdts |
| 6,689,162 | B1 | 2/2004 | Thompson |
| 6,699,274 | B2 | 3/2004 | Stinson |
| 6,702,843 | B1 | 3/2004 | Brown et al. |
| 6,709,454 | B1 | 3/2004 | Cox et al. |
| 6,712,834 | B2 | 3/2004 | Yassour et al. |
| 6,726,700 | B1 | 4/2004 | Levine |
| 6,733,519 | B2 | 5/2004 | Lashinski et al. |
| 6,740,105 | B2 | 5/2004 | Yodfat et al. |
| 6,740,112 | B2 | 5/2004 | Yodfat et al. |
| 6,743,219 | B1 | 6/2004 | Dwyer et al. |
| 6,755,855 | B2 | 6/2004 | Yurek et al. |
| 6,758,885 | B2 | 7/2004 | Leffel et al. |
| 6,767,361 | B2 | 7/2004 | Quiachon et al. |
| 6,773,446 | B1 | 8/2004 | Dwyer et al. |
| 6,793,667 | B2 | 9/2004 | Hebert et al. |
| 6,814,746 | B2 | 11/2004 | Thompson et al. |
| 6,814,748 | B1 | 11/2004 | Baker et al. |
| 6,818,006 | B2 | 11/2004 | Douk et al. |
| 6,833,003 | B2 | 12/2004 | Jones et al. |
| 6,849,084 | B2 | 2/2005 | Rabkin et al. |
| 6,858,034 | B2 | 2/2005 | Hijlkema et al. |
| 6,860,893 | B2 | 3/2005 | Wallace et al. |
| 6,860,898 | B2 | 3/2005 | Stack et al. |
| 6,860,899 | B1 | 3/2005 | Rivelli, Jr. |
| 6,860,900 | B2 | 3/2005 | Clerc et al. |
| 6,860,901 | B1 | 3/2005 | Baker et al. |
| 6,866,677 | B2 | 3/2005 | Douk et al. |
| 6,866,679 | B2 | 3/2005 | Kusleika |
| 6,866,680 | B2 | 3/2005 | Yassour et al. |
| 6,887,267 | B2 | 5/2005 | Dworschak et al. |
| 6,890,337 | B2 | 5/2005 | Feeser et al. |
| 6,893,451 | B2 | 5/2005 | Cano et al. |
| 6,918,921 | B2 | 7/2005 | Brady et al. |

(56) References Cited

U.S. PATENT DOCUMENTS

| | | |
|---|---|---|
| 6,932,837 B2 | 8/2005 | Amplatz et al. |
| 6,936,055 B1 | 8/2005 | Ken et al. |
| 6,955,685 B2 | 10/2005 | Escamilla et al. |
| 6,960,227 B2 | 11/2005 | Jones et al. |
| 6,964,670 B1 | 11/2005 | Shah et al. |
| 6,964,672 B2 | 11/2005 | Brady et al. |
| 6,969,396 B2 | 11/2005 | Krolik et al. |
| 6,976,991 B2 | 12/2005 | Hebert et al. |
| 6,989,024 B2 | 1/2006 | Hebert et al. |
| 6,994,721 B2 | 2/2006 | Israel |
| 7,001,422 B2 | 2/2006 | Escamilla et al. |
| 7,004,962 B2 | 2/2006 | Stinson |
| 7,004,964 B2 | 2/2006 | Thompson et al. |
| 7,011,675 B2 | 3/2006 | Hemerick et al. |
| 7,037,330 B1 | 5/2006 | Rivelli, Jr. et al. |
| 7,041,129 B2 | 5/2006 | Rourke et al. |
| 7,066,951 B2 | 6/2006 | Chobotov |
| 7,069,835 B2 | 7/2006 | Nishri et al. |
| 7,074,236 B2 | 7/2006 | Rabkin et al. |
| 7,093,527 B2 | 8/2006 | Rapaport et al. |
| 7,101,392 B2 | 9/2006 | Heath |
| 7,107,105 B2 | 9/2006 | Bjorklund et al. |
| 7,118,539 B2 | 10/2006 | Vrba et al. |
| 7,118,594 B2 | 10/2006 | Quiachon et al. |
| 7,122,050 B2 | 10/2006 | Randall et al. |
| 7,137,990 B2 | 11/2006 | Hebert et al. |
| 7,166,125 B1 | 1/2007 | Baker et al. |
| 7,169,170 B2 | 1/2007 | Widenhouse |
| 7,169,172 B2 | 1/2007 | Levine et al. |
| 7,172,617 B2 | 2/2007 | Colgan et al. |
| 7,192,434 B2 | 3/2007 | Anderson et al. |
| 7,195,639 B2 | 3/2007 | Quiachon et al. |
| 7,195,648 B2 | 3/2007 | Jones et al. |
| 7,201,768 B2 | 4/2007 | Diaz et al. |
| 7,201,769 B2 | 4/2007 | Jones et al. |
| 7,211,109 B2 | 5/2007 | Thompson |
| 7,213,495 B2 | 5/2007 | McCullagh et al. |
| 7,220,271 B2 | 5/2007 | Clubb et al. |
| 7,235,096 B1 | 6/2007 | Van Tassel et al. |
| 7,264,632 B2 | 9/2007 | Wright et al. |
| 7,275,471 B2 | 10/2007 | Nishri et al. |
| 7,279,005 B2 | 10/2007 | Stinson |
| 7,279,208 B1 | 10/2007 | Goffena et al. |
| 7,294,137 B2 | 11/2007 | Rivelli, Jr. et al. |
| 7,294,146 B2 | 11/2007 | Chew et al. |
| 7,300,456 B2 | 11/2007 | Andreas et al. |
| 7,300,460 B2 | 11/2007 | Levine et al. |
| 7,306,624 B2 | 12/2007 | Yodfat et al. |
| 7,309,351 B2 | 12/2007 | Escamilla et al. |
| 7,311,031 B2 | 12/2007 | McCullagh et al. |
| 7,320,702 B2 | 1/2008 | Hammersmark et al. |
| 7,323,001 B2 | 1/2008 | Clubb et al. |
| 7,331,973 B2 | 2/2008 | Gesswein et al. |
| 7,331,976 B2 | 2/2008 | McGuckin, Jr. et al. |
| 7,331,985 B2 | 2/2008 | Thompson et al. |
| 7,338,518 B2 | 3/2008 | Chobotov |
| 7,438,712 B2 | 10/2008 | Chouinard |
| 7,462,192 B2 | 12/2008 | Norton et al. |
| 7,468,070 B2 | 12/2008 | Henry et al. |
| 7,470,282 B2 | 12/2008 | Shelso |
| 7,473,271 B2 | 1/2009 | Gunderson |
| 7,491,224 B2 | 2/2009 | Cox et al. |
| 7,520,893 B2 | 4/2009 | Rivelli, Jr. |
| RE40,816 E | 6/2009 | Taylor et al. |
| 7,572,288 B2 | 8/2009 | Cox |
| 7,572,290 B2 | 8/2009 | Yodfat et al. |
| 7,588,597 B2 | 9/2009 | Frid |
| 7,695,507 B2 | 4/2010 | Rivelli, Jr. et al. |
| 7,763,011 B2 | 7/2010 | Ortiz et al. |
| 7,771,463 B2 | 8/2010 | Ton et al. |
| 7,854,760 B2 | 12/2010 | Molaei et al. |
| 7,901,447 B2 | 3/2011 | Molaei et al. |
| 7,942,925 B2 | 5/2011 | Yodfat et al. |
| 8,007,529 B2 | 8/2011 | Yan |
| 8,092,486 B2 | 1/2012 | Berrada et al. |
| 8,092,508 B2 | 1/2012 | Leynov et al. |
| 8,192,484 B2 | 6/2012 | Frid |
| 8,382,825 B2 | 2/2013 | Garcia |
| 8,394,119 B2 | 3/2013 | Zaver |
| 8,398,701 B2 | 3/2013 | Berez |
| 2001/0027338 A1 | 10/2001 | Greenberg |
| 2001/0044651 A1 | 11/2001 | Steinke et al. |
| 2001/0049547 A1 | 12/2001 | Moore |
| 2001/0056299 A1 | 12/2001 | Thompson |
| 2002/0004667 A1 | 1/2002 | Adams et al. |
| 2002/0007194 A1 | 1/2002 | Plowiecki |
| 2002/0029061 A1 | 3/2002 | Amplatz et al. |
| 2002/0035396 A1 | 3/2002 | Heath |
| 2002/0062091 A1 | 5/2002 | Jacobsen et al. |
| 2002/0078808 A1 | 6/2002 | Jacobsen et al. |
| 2002/0082558 A1 | 6/2002 | Samson et al. |
| 2002/0087119 A1 | 7/2002 | Parodi |
| 2002/0111633 A1* | 8/2002 | Stoltze et al. .................. 606/108 |
| 2002/0111648 A1 | 8/2002 | Kusleika et al. |
| 2002/0120323 A1 | 8/2002 | Thompson et al. |
| 2002/0138133 A1 | 9/2002 | Lenz et al. |
| 2002/0143361 A1 | 10/2002 | Douk et al. |
| 2002/0169473 A1 | 11/2002 | Sepetka et al. |
| 2002/0169474 A1 | 11/2002 | Kusleika et al. |
| 2002/0173839 A1 | 11/2002 | Leopold et al. |
| 2002/0188314 A1 | 12/2002 | Anderson et al. |
| 2002/0193864 A1 | 12/2002 | Khosravi et al. |
| 2003/0009215 A1 | 1/2003 | Mayer |
| 2003/0023299 A1 | 1/2003 | Amplatz et al. |
| 2003/0069522 A1 | 4/2003 | Jacobsen et al. |
| 2003/0100945 A1 | 5/2003 | Yodfat et al. |
| 2003/0130684 A1 | 7/2003 | Brady et al. |
| 2003/0135258 A1 | 7/2003 | Andreas et al. |
| 2003/0163155 A1 | 8/2003 | Haverkost et al. |
| 2003/0163156 A1 | 8/2003 | Hebert et al. |
| 2003/0176884 A1 | 9/2003 | Berrada et al. |
| 2003/0187495 A1 | 10/2003 | Cully et al. |
| 2003/0212429 A1 | 11/2003 | Keegan et al. |
| 2003/0212430 A1 | 11/2003 | Bose et al. |
| 2004/0024416 A1 | 2/2004 | Yodfat et al. |
| 2004/0030265 A1 | 2/2004 | Murayama et al. |
| 2004/0044395 A1 | 3/2004 | Nelson |
| 2004/0073300 A1 | 4/2004 | Chouinard et al. |
| 2004/0088037 A1 | 5/2004 | Nachreiner et al. |
| 2004/0093010 A1 | 5/2004 | Gesswein et al. |
| 2004/0098099 A1 | 5/2004 | McCullagh et al. |
| 2004/0133223 A1 | 7/2004 | Weber |
| 2004/0153117 A1 | 8/2004 | Clubb et al. |
| 2004/0162606 A1 | 8/2004 | Thompson |
| 2004/0172055 A1 | 9/2004 | Huter et al. |
| 2004/0186368 A1 | 9/2004 | Ramzipoor et al. |
| 2004/0193178 A1 | 9/2004 | Nikolchev |
| 2004/0193179 A1 | 9/2004 | Nikolchev |
| 2004/0193208 A1 | 9/2004 | Talpade et al. |
| 2004/0199243 A1 | 10/2004 | Yodfat |
| 2004/0210235 A1 | 10/2004 | Deshmukh et al. |
| 2004/0215332 A1 | 10/2004 | Frid |
| 2004/0220585 A1 | 11/2004 | Nikolchev |
| 2004/0220608 A1 | 11/2004 | D'Aquanni et al. |
| 2004/0220663 A1 | 11/2004 | Rivelli |
| 2004/0254628 A1 | 12/2004 | Nazzaro et al. |
| 2004/0260331 A1 | 12/2004 | D'Aquanni et al. |
| 2005/0004595 A1 | 1/2005 | Boyle et al. |
| 2005/0021075 A1 | 1/2005 | Bonnette et al. |
| 2005/0033407 A1 | 2/2005 | Weber et al. |
| 2005/0038447 A1 | 2/2005 | Huffmaster |
| 2005/0051243 A1 | 3/2005 | Forbes Jones et al. |
| 2005/0055047 A1 | 3/2005 | Greenhalgh |
| 2005/0059889 A1 | 3/2005 | Mayer |
| 2005/0060017 A1 | 3/2005 | Fischell et al. |
| 2005/0090888 A1 | 4/2005 | Hines et al. |
| 2005/0101989 A1 | 5/2005 | Cully et al. |
| 2005/0137680 A1 | 6/2005 | Ortiz et al. |
| 2005/0149111 A1 | 7/2005 | Kanazawa et al. |
| 2005/0165441 A1 | 7/2005 | McGuckin et al. |
| 2005/0177186 A1 | 8/2005 | Cully et al. |
| 2005/0192620 A1 | 9/2005 | Cully et al. |
| 2005/0209672 A1 | 9/2005 | George et al. |
| 2005/0209678 A1 | 9/2005 | Henkes et al. |

(56) References Cited

U.S. PATENT DOCUMENTS

| | | |
|---|---|---|
| 2005/0246010 A1 | 11/2005 | Alexander et al. |
| 2005/0267568 A1 | 12/2005 | Berez et al. |
| 2005/0283220 A1 | 12/2005 | Gobran et al. |
| 2005/0288764 A1 | 12/2005 | Snow et al. |
| 2005/0288766 A1 | 12/2005 | Plain et al. |
| 2006/0020324 A1 | 1/2006 | Schmid et al. |
| 2006/0036309 A1 | 2/2006 | Hebert et al. |
| 2006/0089703 A1 | 4/2006 | Escamilla et al. |
| 2006/0095213 A1 | 5/2006 | Escamilla et al. |
| 2006/0111771 A1 | 5/2006 | Ton et al. |
| 2006/0116713 A1 | 6/2006 | Sepetka et al. |
| 2006/0116750 A1 | 6/2006 | Hebert et al. |
| 2006/0184238 A1 | 8/2006 | Kaufmann et al. |
| 2006/0195118 A1 | 8/2006 | Richardson |
| 2006/0206148 A1 | 9/2006 | Khairkhahan et al. |
| 2006/0206200 A1 | 9/2006 | Garcia et al. |
| 2006/0206201 A1 | 9/2006 | Garcia et al. |
| 2006/0212127 A1 | 9/2006 | Karabey et al. |
| 2006/0271149 A1 | 11/2006 | Berez et al. |
| 2006/0271153 A1 | 11/2006 | Garcia et al. |
| 2007/0021816 A1 | 1/2007 | Rudin |
| 2007/0043419 A1 | 2/2007 | Nikolchev et al. |
| 2007/0055365 A1 | 3/2007 | Greenberg et al. |
| 2007/0060994 A1 | 3/2007 | Gobran et al. |
| 2007/0073379 A1 | 3/2007 | Chang |
| 2007/0077347 A1 | 4/2007 | Richter |
| 2007/0100321 A1 | 5/2007 | Rudakov et al. |
| 2007/0100414 A1 | 5/2007 | Licata et al. |
| 2007/0100430 A1 | 5/2007 | Rudakov et al. |
| 2007/0112415 A1 | 5/2007 | Bartlett |
| 2007/0119295 A1 | 5/2007 | McCullagh et al. |
| 2007/0123969 A1 | 5/2007 | Gianotti |
| 2007/0162104 A1 | 7/2007 | Frid |
| 2007/0167980 A1 | 7/2007 | Figulla et al. |
| 2007/0198076 A1 | 8/2007 | Hebert et al. |
| 2007/0203559 A1 | 8/2007 | Freudenthal et al. |
| 2007/0203563 A1 | 8/2007 | Hebert et al. |
| 2007/0208367 A1 | 9/2007 | Fiorella et al. |
| 2007/0208373 A1 | 9/2007 | Zaver et al. |
| 2007/0208376 A1 | 9/2007 | Meng |
| 2007/0208415 A1 | 9/2007 | Grotheim et al. |
| 2007/0225760 A1 | 9/2007 | Moszner et al. |
| 2007/0233175 A1 | 10/2007 | Zaver et al. |
| 2007/0239261 A1 | 10/2007 | Bose et al. |
| 2007/0255386 A1 | 11/2007 | Tenne |
| 2007/0255388 A1 | 11/2007 | Rudakov et al. |
| 2007/0280850 A1 | 12/2007 | Carlson |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0015673 A1 | 1/2008 | Chuter |
| 2008/0033341 A1 | 2/2008 | Grad |
| 2008/0033526 A1* | 2/2008 | Atladottir et al. ............ 623/1.11 |
| 2008/0039930 A1 | 2/2008 | Jones et al. |
| 2008/0039933 A1 | 2/2008 | Yodfat et al. |
| 2008/0082154 A1 | 4/2008 | Tseng et al. |
| 2008/0114391 A1 | 5/2008 | Dieck et al. |
| 2008/0125855 A1 | 5/2008 | Henkes et al. |
| 2008/0208320 A1 | 8/2008 | Tan-Malecki et al. |
| 2008/0221666 A1 | 9/2008 | Licata et al. |
| 2008/0221670 A1 | 9/2008 | Clerc et al. |
| 2008/0221671 A1 | 9/2008 | Chouinard et al. |
| 2008/0255654 A1 | 10/2008 | Hebert et al. |
| 2008/0255655 A1 | 10/2008 | Kusleika et al. |
| 2008/0262590 A1 | 10/2008 | Murray |
| 2008/0269774 A1 | 10/2008 | Garcia et al. |
| 2008/0275497 A1 | 11/2008 | Palmer et al. |
| 2008/0275498 A1 | 11/2008 | Palmer et al. |
| 2008/0294104 A1 | 11/2008 | Mawad |
| 2008/0300667 A1 | 12/2008 | Hebert et al. |
| 2009/0024202 A1 | 1/2009 | Dave et al. |
| 2009/0024205 A1 | 1/2009 | Hebert et al. |
| 2009/0030496 A1 | 1/2009 | Kaufmann et al. |
| 2009/0030497 A1 | 1/2009 | Metcalf et al. |
| 2009/0054981 A1 | 2/2009 | Frid et al. |
| 2009/0099643 A1 | 4/2009 | Hyodoh et al. |
| 2009/0105802 A1 | 4/2009 | Henry et al. |
| 2009/0105803 A1 | 4/2009 | Shelso |
| 2009/0125093 A1 | 5/2009 | Hansen |
| 2009/0192536 A1 | 7/2009 | Berez et al. |
| 2009/0192587 A1 | 7/2009 | Frid |
| 2009/0198318 A1 | 8/2009 | Berez et al. |
| 2009/0216307 A1* | 8/2009 | Kaufmann et al. ............ 623/1.3 |
| 2009/0270974 A1 | 10/2009 | Berez et al. |
| 2009/0287241 A1 | 11/2009 | Berez et al. |
| 2009/0287288 A1 | 11/2009 | Berez et al. |
| 2009/0288000 A1 | 11/2009 | McPherson |
| 2009/0292348 A1 | 11/2009 | Berez et al. |
| 2009/0318947 A1 | 12/2009 | Garcia et al. |
| 2009/0319017 A1 | 12/2009 | Berez et al. |
| 2010/0010624 A1 | 1/2010 | Berez et al. |
| 2010/0061604 A1 | 3/2010 | Nahm et al. |
| 2010/0063531 A1 | 3/2010 | Rudakov et al. |
| 2010/0076317 A1 | 3/2010 | Babic et al. |
| 2010/0152834 A1 | 6/2010 | Hannes et al. |
| 2010/0174269 A1 | 7/2010 | Tompkins et al. |
| 2010/0174309 A1 | 7/2010 | Fulkerson et al. |
| 2010/0179583 A1 | 7/2010 | Carpenter et al. |
| 2010/0179647 A1 | 7/2010 | Carpenter et al. |
| 2010/0198334 A1 | 8/2010 | Yodfat et al. |
| 2010/0204779 A1 | 8/2010 | Schuessler et al. |
| 2010/0222864 A1 | 9/2010 | Rivelli, Jr. et al. |
| 2010/0256733 A1 | 10/2010 | Schuessler |
| 2010/0280587 A1 | 11/2010 | Ortiz et al. |
| 2010/0318174 A1 | 12/2010 | Shaolian et al. |
| 2010/0318178 A1 | 12/2010 | Rapaport et al. |
| 2011/0016427 A1 | 1/2011 | Douen |
| 2011/0040372 A1 | 2/2011 | Hansen et al. |
| 2011/0046718 A1 | 2/2011 | Cattaneo et al. |
| 2011/0046720 A1 | 2/2011 | Shalev et al. |
| 2011/0166592 A1 | 7/2011 | Garcia et al. |
| 2011/0179389 A1 | 7/2011 | Douen |
| 2011/0184451 A1 | 7/2011 | Sahl |
| 2011/0190862 A1 | 8/2011 | Bashiri et al. |
| 2011/0245862 A1 | 10/2011 | Dieck et al. |
| 2011/0270178 A1 | 11/2011 | Fiorella et al. |
| 2012/0035643 A1 | 2/2012 | Khairkhahan et al. |
| 2012/0041459 A1 | 2/2012 | Fiorella et al. |
| 2012/0158124 A1 | 6/2012 | Zaver et al. |
| 2012/0253454 A1 | 10/2012 | Costello |
| 2012/0290067 A1 | 11/2012 | Cam et al. |
| 2012/0316638 A1 | 12/2012 | Grad et al. |
| 2012/0323309 A1 | 12/2012 | Cattaneo |
| 2013/0123901 A1* | 5/2013 | Connor et al. ............... 623/1.15 |
| 2013/0172975 A1 | 7/2013 | Berez et al. |

FOREIGN PATENT DOCUMENTS

| | | |
|---|---|---|
| EP | 1683541 A2 | 7/2006 |
| EP | 1942972 | 7/2008 |
| EP | 1872742 B1 | 5/2009 |
| EP | 2 078 512 A1 | 7/2009 |
| FR | 2556210 | 6/1985 |
| FR | 2556210 B1 | 4/1988 |
| JP | 10-328216 A | 12/1998 |
| JP | 11-506686 | 6/1999 |
| JP | 11-299901 A | 11/1999 |
| JP | 2001-509412 A | 7/2001 |
| JP | 2002-253682 | 9/2002 |
| JP | 2003520103 | 7/2003 |
| JP | 2004-049585 A | 2/2004 |
| JP | 2005-074230 A | 3/2005 |
| JP | 2006-506201 A | 2/2006 |
| JP | 2008-541832 A | 11/2008 |
| JP | 4673987 B2 | 4/2011 |
| WO | WO-88/00813 | 2/1988 |
| WO | WO-95/09586 | 4/1995 |
| WO | WO-95/32757 | 12/1995 |
| WO | WO-98/04211 | 2/1998 |
| WO | 98/47447 A1 | 10/1998 |
| WO | WO-99/02092 | 1/1999 |
| WO | 99/05977 A1 | 2/1999 |
| WO | WO-99/49812 A3 | 12/1999 |
| WO | WO-01/05331 | 1/2001 |

(56) References Cited

FOREIGN PATENT DOCUMENTS

| WO | WO-01/52771 | 7/2001 |
|---|---|---|
| WO | WO-02/05729 | 1/2002 |
| WO | WO-02/47579 | 6/2002 |
| WO | WO-02/054988 A3 | 1/2003 |
| WO | WO-03/007840 A2 | 1/2003 |
| WO | WO-03/043527 A2 | 5/2003 |
| WO | WO-03/049600 A2 | 6/2003 |
| WO | 03/057079 A1 | 7/2003 |
| WO | WO-03/073963 A2 | 9/2003 |
| WO | WO-2004/087006 A3 | 11/2004 |
| WO | WO 2005/021061 | 3/2005 |
| WO | WO-2005/023149 A3 | 12/2005 |
| WO | 2006/034140 A2 | 3/2006 |
| WO | WO-2006/073745 A2 | 7/2006 |
| WO | WO-2006/127005 | 11/2006 |
| WO | 2007/122396 A1 | 11/2007 |
| WO | 2008/005898 A2 | 1/2008 |
| WO | WO-2007/139689 A3 | 9/2008 |
| WO | WO-2007/139699 A3 | 9/2008 |
| WO | WO 2008/156683 | 12/2008 |
| WO | WO-2005/115118 A3 | 7/2009 |
| WO | WO-2009/105710 | 8/2009 |
| WO | 2010/127838 A2 | 11/2010 |
| WO | 2011/023105 A1 | 3/2011 |
| WO | 2011/134663 A2 | 11/2011 |

OTHER PUBLICATIONS

Brilstra, et al., Treatment of Intracranial Aneurysms by Embolization with Coils: A Systematic Review, Stroke, Journal of the American Heart Association, 1999, vol. 30, pp. 470-476.

Ferguson, Gary, Physical Factors in the Initiation, Growth and Rupture of Human Intracranial Saccular Aneurysms, J. Neurosurg, Dec. 1972, vol. 37, pp. 666-667.

Geremia, et al., Embolization of Experimentally Created Aneurysms with Intravascular Stent Devices, ANJR American Journal of Neuroradiology, Aug. 1994, vol. 15, pp. 1223-1231.

Geremia, et al., Occlusion of Experimentally Created Fusiform Aneurysms with Porous Metallic Stents, ANJR Am J Neuroradiol, Apr. 2000, Issue 21, pp. 739-745.

Lanzino, et al., Efficacy and Current Limitations of Intravascular Stents for Intracranial Internal Carotid, Vertebral, and Basilar Artery Aneurysms, Journal of Neurosurgery, Oct. 1999, vol. 91, Issue 4, pp. 538-546.

Lieber, et al., Alteration of Hemodynamics in Aneurysm Models by Stenting: Influence of Stent Porosity, Ann of Biomedical Eng., 1997, vol. 25, pp. 460-469, Buffalo, NY.

Lieber, et al., The Physics of Endoluminal Stenting in the Treatment of Cerebrovascular Aneurysms, Neurological Research, 2002, Vcol 24, Issue Supplement 1, pp. S32-S42.

Moss, et al., Vascular Occlusion with a Balloon-Expadable Stent Occluder, Radiology, May 1994, vol. 191, Issue 2, pp. 483-486.

Pereira, Edgard, History of Endovascular Aneurysm Occlusion, Management of Cerebral Aneurysms, 2004, pp. 11-26.

Qureshi, Adnan, Endovascular Treatment of Cerebrovascular Diseases and Intracranial Neoplasms, The Lancelet, Mar. 2004, vol. 363, pp. 804-813.

Steiger, Pathophysiology of Development and Rupture of Cerebral Aneurysms, Acta Nurochirurgica, Mar. 1990, vol. Supplementum 48, Pages in 62 pages.

Tenaglia, et al., Ultrasound Guide Wire-Directed Stent Deployment, Duke University Medical Center, Department of Medicine, 1993 USA.

Yu, et al., A Steady Flow Analysis on the Stented and Non-Stented Sidewall Aneurysm Models, Medical Engineering and Physics, Apr. 1999, Issue 21, pp. 133-141.

U.S. Appl. No. 13/644,854, filed Oct. 31, 2012.
U.S. Appl. No. 13/669,944, filed Nov. 6, 2012.
U.S. Appl. No. 13/826,971, filed Mar. 14, 2013.
U.S. Appl. No. 13/775,592, filed Feb. 25, 2013.
U.S. Appl. No. 13/845,162, filed Mar. 18, 2013.
U.S. Appl. No. 13/827,030, filed Mar. 14, 2013.
U.S. Appl. No. 13/826,147, filed Mar. 14, 2013.

* cited by examiner

METHODS FOR ATTAINING A PREDETERMINED POROSITY OF A VASCULAR DEVICE

CROSS-REFERENCE TO RELATED APPLICATIONS

This application claims priority to U.S. Provisional Patent Application Ser. No. 61/720,154, filed Oct. 30, 2012, which is incorporated herein by reference in its entirety.

BACKGROUND

Lumens in a patient's body can change in size, shape, and/or patency, and such changes can present complications or affect associated bodily functions. For example, the walls of the vasculature, particularly arterial walls, may develop a pathological dilatation, commonly called an aneurysm. Aneurysms are observed as a ballooning-out of the wall of an artery. This is a result of the vessel wall being weakened by disease, injury, or a congenital abnormality. Aneurysms have thin, weak walls and have a tendency to rupture and are often caused or made worse by high blood pressure. Aneurysms can be found in different parts of the body; the most common being abdominal aortic aneurysms (AAA) and the brain or cerebral aneurysms. The mere presence of an aneurysm is not always life-threatening, but an aneurysm can have serious health consequences such as a stroke if one should rupture in the brain. Additionally, a ruptured aneurysm can also result in death.

SUMMARY

The subject technology is illustrated, for example, according to various aspects described below. Various examples of aspects of the subject technology are described as numbered clauses (1, 2, 3, etc.) for convenience. These are provided as examples, and do not limit the subject technology. It is noted that any of the dependent clauses may be combined in any combination, and placed into a respective independent clause, e.g., clause 1, 16 and 23. The other clauses can be presented in a similar manner.

1. A method for manufacturing a vascular device, comprising:
disposing a vascular device over an expanding member, the device comprising a body having a substantially uniform porosity that is adapted to change by adjusting an axial length of the body; and
adhering a portion of the body to the expanding member such that upon radial expansion of the expanding member, adherence between the body portion and the expanding member reduces a porosity of the body within the body portion more than the body porosity is reduced outside the portion.

2. The method of clause 1, wherein the adhering occurs when the expanding member is in an expanded configuration.

3. The method of clause 2, wherein the expanding member in the expanded configuration is uniformly stretched when unrestrained.

4. The method of clause 1, wherein the adhering occurs when the expanding member is in a collapsed configuration.

5. The method of clause 1, wherein the adherence between the body portion and the expanding member is configured to sever upon at least partial expansion of the expanding member.

6. The method of clause 1, wherein the adherence between the body portion and the expanding member is configured to sever when the expanding member is expanded to more than 80% the expanding member's fully expanded configuration.

7. The method of clause 1, wherein the adherence between the body portion and the expanding member is configured to sever due to shear strain in the adherence upon expansion of the expanding member.

8. A method for manufacturing a vascular device, comprising:
aligning a region of a vascular device with an area of an expanding member, the device having a porosity that is altered by adjustment of an axial length of the device; and
adhering the region of the device to the area of the expanding member such that upon radial expansion of the expanding member, adherence between the device and the expanding member reduces a porosity of the region more than the porosity is reduced outside the region.

9. The method of clause 8, wherein the adhering occurs when the expanding member is in a radially expanded configuration.

10. The method of clause 8, wherein the adhering occurs when the expanding member is in a collapsed configuration.

11. The method of clause 8, wherein the adherence between the region of the device and the area of the expanding member is configured to sever upon at least partial expansion of the expanding member.

12. The method of clause 8, wherein the adherence between the region of the device and the area of the expanding member is configured to sever when the expanding member is expanded to more than 80% the expanding member's fully expanded configuration.

13. The method of clause 8, wherein the adherence between the region of the device and the area of the expanding member is configured to sever due to shear strain in the adherence upon expansion of the expanding member.

14. A method for treating an aneurysm, the method comprising:
positioning a vascular device in a vessel at an ostium of the aneurysm, the device comprising a body having a substantially uniform porosity that is adapted to change by adjusting an axial length of the body;
inflating an expanding member positioned within a central lumen of the body; and reducing a porosity of the body within a body region more than the body porosity is reduced outside the region as the body is radially expanded, by engaging the body with the expanding member.

15. The method of clause 14, wherein the positioning comprises axially offsetting the region from the ostium of the aneurysm prior to expanding the device.

16. The method of clause 14, further comprising reducing an axial length of the expanding member by axially collapsing a corrugated tube positioned within the expanding member.

17. The method of clause 14, further comprising dissolving an adhesive that bonds a portion of the body to the expanding member.

18. The method of clause 14, further comprising expanding the body, wherein the body comprises a self-expanding braided structure or cut metal tube.

19. The method of clause 14, wherein an axial length of the expanding member in a collapsed configuration is about 200-500% longer than the axial length of the expanding member in a radially expanded configuration.

20. The method of clause 19, wherein a change in the axial length of the expanding member from the collapsed configuration to the expanded configuration is the same as a change in the axial length of the body from a body collapsed configuration to a body expanded configuration.

21. A method for treating an aneurysm, the method comprising:

positioning a vascular device in a vessel at an ostium of the aneurysm, the device having a porosity that is altered by adjustment of an axial length of the device;

expanding an expanding member positioned within a lumen of the device; and reducing a porosity of the device within a region more than the porosity is reduced outside the region by axially shortening the region with the expanding member.

22. The method of clause 21, wherein the positioning comprises axially offsetting the region from the ostium of the aneurysm prior to expanding the expanding member.

23. The method of clause 21, further comprising reducing an axial length of the expanding member by axially collapsing a corrugated tube positioned within the expanding member.

24. The method of clause 21, further comprising dissolving an adhesive that bonds a portion of the device to a portion of the expanding member.

25. The method of clause 21, wherein an axial length of the expanding member in a collapsed configuration is about 200-500% longer than the axial length of the expanding member in an expanded configuration.

26. The method of clause 25, wherein a change in the axial length of the expanding member from the collapsed configuration to the expanded configuration is the same as a change in the axial length of the device from a device collapsed configuration to a device expanded configuration.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

A detailed description will be made with reference to the accompanying drawings.

DETAILED DESCRIPTION

Figure 1A:
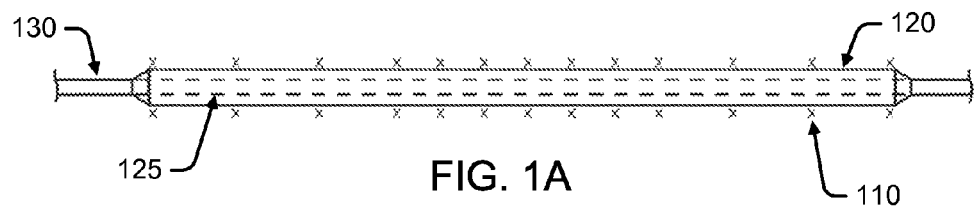
FIG. 1A depicts a system for controllably deploying a vascular device in a collapsed configuration, according to some embodiments of the subject technology.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology.

Aneurysms may be located, for example, along vessel side walls. A neck of an aneurysm typically defines an opening of between about 2 to 25 mm, though other sizes and ranges are also possible. The neck connects an anatomical lumen to a fundus of the aneurysm. In some embodiments, "vessel" or "lumen" may refer to blood vessels (including arteries and veins) or other suitable body organs having a lumen, such as the gastrointestinal tract (e.g., esophagus, stomach, small intestine, colon, rectum), bile ducts, urinary bladder, ureter, urethra, trachea, bronchi, and the like. Blood flow within the anatomical lumen flows through the neck and into the fundus. In response to the constant blood flow into the fundus of the aneurysm, the wall of the aneurysm continues to distend and presents a significant risk of rupturing. When the blood within the aneurysm causes pressure against the wall of the aneurysm that exceeds the wall strength, the aneurysm ruptures.

Reduction of blood flow to or within the aneurysm results in a reduction in force against the wall of the aneurysm and a corresponding reduction in the risk of rupturing. A reduction of the force and volume of blood entering the aneurysm may be accomplished by an occluding device. Occluding devices may be dependent on a physician's skill during deployment, to ensure that a desired porosity is attained at the neck of the aneurysm. If the porosity too high at the neck, then the occluding device may fail in sufficiently reducing the blood flow into the fundus. The porosity of some occluding devices may be reduced by applying a longitudinally compressive force to a proximal portion of the occluding device towards the direction of a distal portion. Because the porosity of the occluding device may be modified by application of the compressive force, achieving the desired porosity consistently and reliably is heavily dependant on physician skill.

The methods and systems of the subject technology solve some or all of the foregoing problems by controlling the deployment of a vascular device such that the device occludes blood flow into the aneurysm consistently and reliably, to thereby prevent or reduce likelihood of aneurysm ruptures. The system includes an expandable vascular device and an expanding member positioned within a central lumen of the vascular device. The expanding member is configured to attain a predetermined porosity for a region of the device during deployment. Accordingly, controlling the deployment of the vascular device using the expanding member to attain the predetermined porosity for the region, reduces or stops the laminar flow into the aneurysm, thereby allowing the blood within the aneurysm to begin to stagnate. Stagnation of blood, as opposed to continuous flow through a fundus of the aneurysm, results in thrombosis in the aneurysm, which also helps protect the aneurysm from rupturing.

Figure 1B:
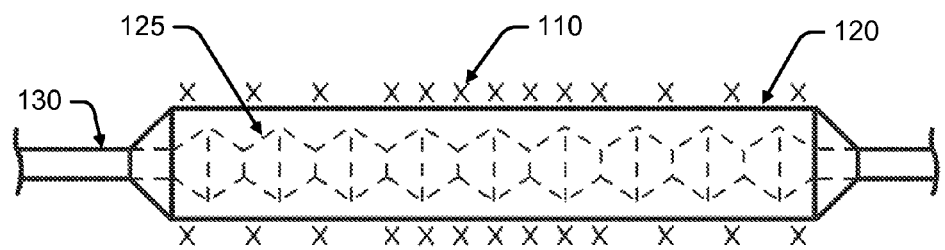
FIG. 1B depicts a system for controllably deploying a vascular device in an intermediate configuration, according to some embodiments of the subject technology.
Figure 1C:
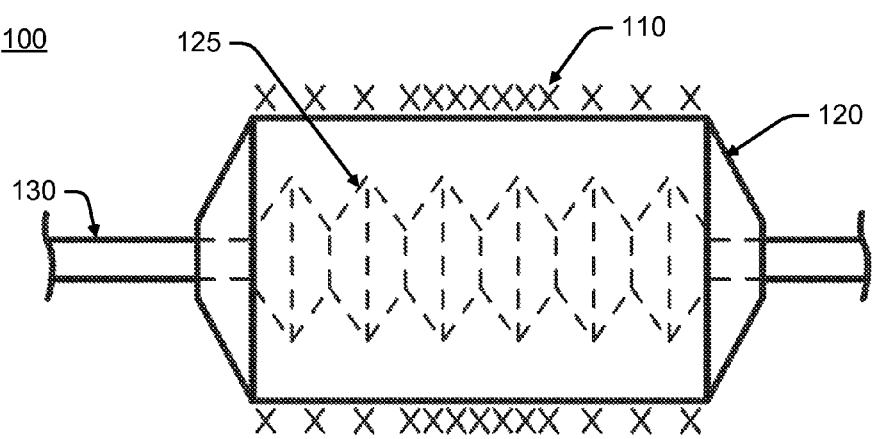
FIG. 1C depicts a system for controllably deploying a vascular device in an expanded configuration, according to some embodiments of the subject technology.

FIGS. 1A-1C depict a system 100 for controllably deploying a vascular device 110, according to some embodiments of the subject technology. The system 100 includes an expandable vascular device 110, an expanding member 120 positioned within a central lumen of the vascular device 110, and a catheter 130.

Figure 2:
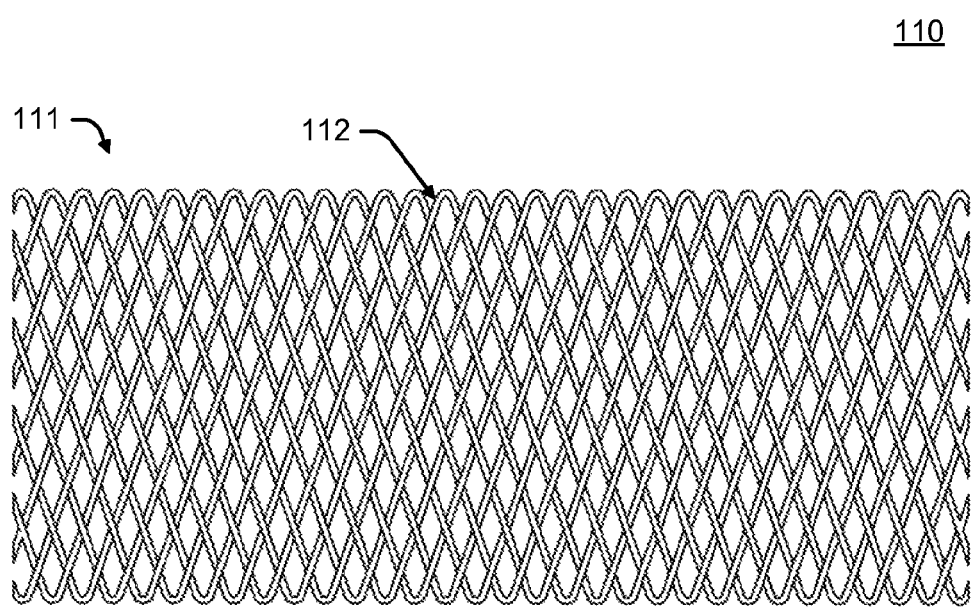
FIG. 2 depicts a vascular device, according to some embodiments of the subject technology.

Referring to FIG. 2, the vascular device 110 comprises a body 111 having a substantially uniform porosity. The body 111 may be formed of a plurality of substantially uniformly spaced members 112. The porosity of the body 111 is adapted to change by adjusting an axial length of the body 111. For example, the body 111 may be configured to decrease in porosity as a result of being axially shortened during and/or after diametrical, or radial, expansion. The body 111 may be a self-expanding stent made of two or more round or ovoid wire filaments 112. Accordingly, the body 111 has a first, collapsed configuration, and a second, expanded configuration. The filaments 112 may be formed of known flexible materials including shape memory materials, such as nitinol, platinum and stainless steel. The body 111 may be fabricated from platinum/8% tungsten and 35N LT (cobalt nickel alloy, which is a low titanium version of MP35N alloy) alloy wires. In other embodiments, one or more of the filaments 112 can be formed of a biocompatible metal material or a biocompatible polymer. The filaments 112 may be braided into a resulting lattice-like structure. In at least one embodiment, during braiding or winding of the body 111, the filaments 112 may be loosely braided using a 1-over-2-under-2 system. In other embodiments, however, other methods of braiding may be followed, without departing from the scope of the disclosure.

Alternatively, the body 111 may be formed, for example, by laser cutting a pre-formed tube or sheet, by interconnecting a multitude of members 112 by laser welding, or by other suitable methods such as electrochemical etching, grinding, piercing, electroforming, or other means. In another example, the body 111 may comprise a tubular stent.

The body 111 has a porosity configured to reduce haemodynamic flow into, for example, an aneurysm. The porosity of the body 111, determined by the plurality of members 112, may be adjusted by axially shortening the body 111. The ends of the body 111 may be cut to length and therefore remain free for radial expansion and contraction. The body 111 may exhibit a high degree of flexibility due to the materials used, the porosity of the body 111, and the fact that the ends are not secured.

Referring to FIGS. 1A-1C, the expanding member 120 is configured to engage the body 111 of the vascular device 110, as the body 111 is expanded from the first, collapsed configuration. The expanding member 120 may comprise an elastomeric balloon capable of being very elastic, such that an axial length of the expanding member 120 in a collapsed configuration is about 200-500% longer than the axial length of the expanding member 120 in an expanded configuration. The expanding member 120 may be formed from polyurethane, silicone, or other similar materials.

The expanding member 120 is configured to geometrically deform in a similar manner as the vascular device 110, as the body 111 moves from the first, collapsed configuration to the second, expanded configuration. For example, during expansion of the expanding member 120 from the collapsed configuration to the expanded configuration, the expanding member 120 may be configured to shorten in axial length and increase in radial dimension, or diameter, by the same amounts as the body 111 does when the body 111 moves from the first, collapsed configuration to the second, expanded configuration. In other words, a change in the axial length and radial dimension of the expanding member 120 from the collapsed configuration to the expanded configuration is the same as a change in the axial length and radial dimension of the body 111 from the first, collapsed configuration to the second, expanded configuration.

The expanding member 120 may have an inner member 125 disposed within a central longitudinal axis of the expanding member 120 that is configured to axially shorten during expansion or inflation of the expanding member 120. The inner member 125 may be configured to axially shorten by the same amount as the expanding member 120 axially shortens during expansion or inflation. The inner member 125 may, for example, comprise a corrugated tube, telescoping tube, or other structure configured to axially shorten or collapse. A proximal and distal end of the expanding member 120 may be attached, coupled, or adhered to a proximal and distal portion of the inner member 125.

In some aspects, to reduce the tendency of the expanding member 120 to creep or stress relax, the material of the expanding member 120 may be cross-linked. Cross-links are bonds, bi-functional polymer chains or multi-functional polymer chains that link one polymer chain of the expanding member 120 material to another. Cross-links can be formed by chemical reactions that are initiated by heat, pressure, change in pH, radiation, or other means. For example, mixing of an unpolymerized or partially polymerized resin with specific chemicals called cross-linking reagents results in a chemical reaction that forms cross-links between the polymer chains of the expanding member 120 material. If further protection from creep or stress relaxation is desired, the expanding member 120 could be shipped in an axially shortened and radially expanded configuration, or in the expanded configuration. In this example, the expanding member 120 may be configured to be "at rest" when the expanding member 120 is at its largest diameter and its shortest length.

Referring to FIGS. 3A-3D, the expanding member 120 may be manufactured using molds 310. In this process, a length of polymer tubing (parison) 320 is placed into the mold. Heater elements bring the parison to the working temperature and the parison is then axially stretched and internally pressurized "P" to form the expanding member 120. Using this process, the expanding member 120 may have varying cross sectional shapes either along the expanding member 120 length or normal to the expanding member 120 longitudinal axis, or both. This expanding member 120 manufacturing process may impart axial or biaxial orientation to the polymer chains of which the expanding member 120 may be comprised.

Alternatively, the expanding member 120 may be manufactured by solution casting. Solution casting is a process in which the mold is rotated, causing a solution in the mold to conform to the interior surface of the mold due to centrifugal force. After the solution has cured into a film, the mold is disassembled, thereby releasing the expanding member 120.

Other known methods may also be used to manufacture the expanding member 120. In some examples the expanding member 120 is comprised of wound or braided filaments imbedded in the elastomeric polymer. In another example the expanding member 120 may be comprised of braided filaments which can be axially lengthened or shortened using a telescoping rod and tube, the rod being attached to distal ends of the braided filaments and the tube being attached to proximal ends of the braided filaments.

Figure 3A:
FIG. 3A depicts a parison used for manufacturing an expanding member, according to sonic embodiments of the subject technology.
Figure 3B:
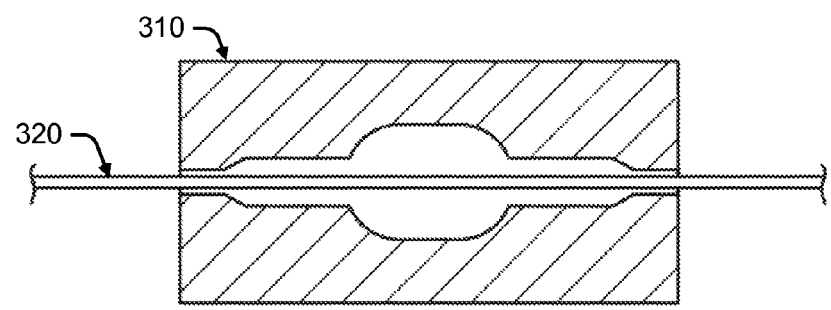
FIG. 3B depicts an example process for manufacturing an expanding member, according to some embodiments of the subject technology.
Figure 3C:
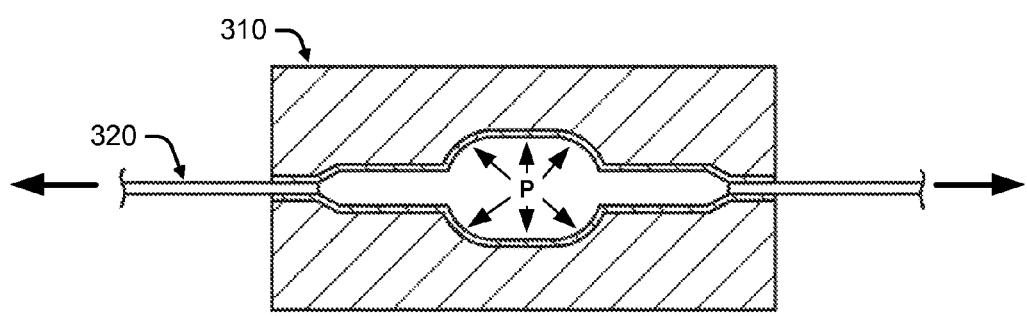
FIG. 3C depicts an example process for manufacturing an expanding member, according to some embodiments of the subject technology.
Figure 3D:
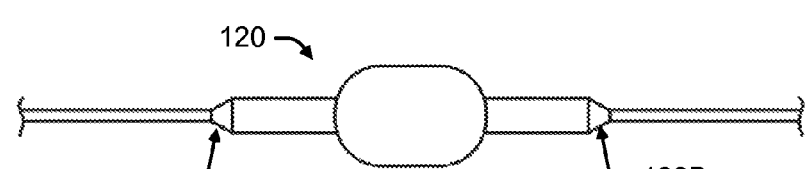
FIG. 3D depicts an expanding member, according to some embodiments of the subject technology.
Figure 3E:
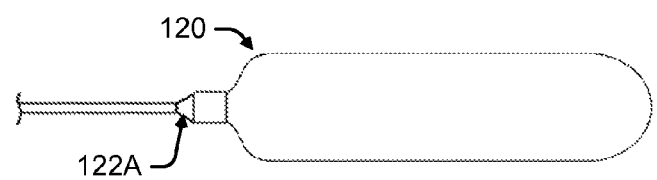
FIG. 3E depicts an expanding member, according to some embodiments of the subject technology.

The expanding member 120 may have a proximal cuff 122A and a distal cuff 122B for attachment to a catheter 130. In another embodiment, the expanding member 120 may only have a proximal cuff 122A, as shown in FIG. 3E. This embodiment is particularly useful for attaching to a distal end of a fixed wire catheter, as discussed further below.

FIGS. 4A-7B depict the vascular device 110 and the expanding member 120, according to some embodiments of the subject technology. The expanding member 120 is positioned within the central lumen of the vascular device 110 before and during deployment of the vascular device 110 within a patient's vasculature. The expanding member 120 may be configured to controllably expand the vascular device 110 such that the vascular device 110 attains a predetermined porosity at a particular region, such as near a treatment site which may be near a neck of an aneurysm. For example, during deployment, the expanding member 120 may cause a reduction in a porosity of the body 111 within a region 115A-D that is more than the reduction of the porosity of the body 111 outside the region 115A-D, thereby attaining a predetermined porosity for the region 115A-D.

Alternatively, the expanding member 120 may be configured to controllably expand the vascular device 110 such that the vascular device 110 attains a predetermined porosity in more than one region, such as proximal and distal to the neck of the aneurysm where pressure may be higher.

Referring to FIGS. 4A-4D, the expanding member 120 may controllably expand the vascular device 110 and attain the predetermined porosity for the region 115A by positively engaging a portion of the vascular device 110 before and during deployment. For example, an adhesive 117 may be used to positively engage, couple, attach, or adhere a portion of the vascular device 110 to an outer surface of the expanding member 120. The adhesive 117 assists in utilizing the axial shrinkage and radial expansion characteristics of the expanding member 120 to control the porosity of the vascular device 110 by positively engaging, coupling, attaching, or adhering the expanding member 120 to the vascular device 110.

The adhesive 117 may comprise biodegradable materials, or materials that dissolve in the body or in the bloodstream. For example, the adhesive 117 may include sugar, carbowax, polyethylene oxide, poly vinyl alcohol, poly lactic acid (PLA), poly glycolic acid (PGA), poly lactic glycolic acid (PLGA), poly(e-caprolactone) copolymers, polydioxanone, polypropylene fumarate) poly(trimethylene carbonate) copolymers, polyhydroxy alkanoates, polyphosphazenes, polyanhydrides, poly(ortho esters), poly(amino acids), or "pseudo"-poly(amino acids).

In some aspects, the expanding member 120 may be configured to allow perfusion of tissues downstream of the expanding member during expansion or inflation of the expanding member 120. Allowing perfusion of tissues downstream also aids in dissolution of the adhesive 117.

Figure 4A:
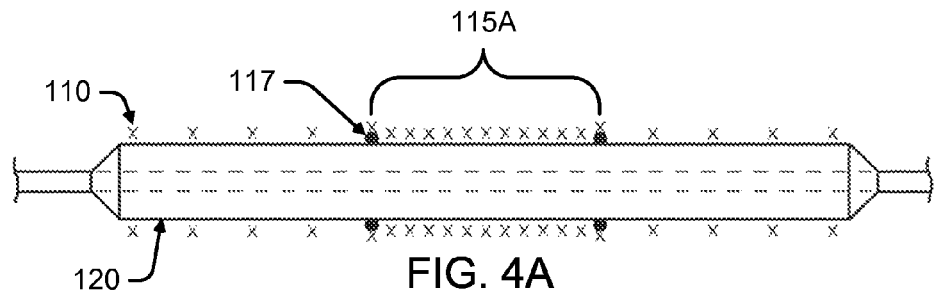
FIG. 4A depicts a vascular device coupled to an expanding member using an adhesive, according to some embodiments of the subject technology.
Figure 4B:
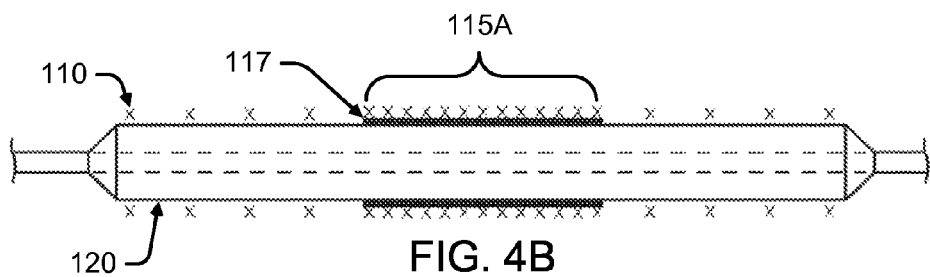
FIG. 4B depicts a vascular device coupled to an expanding member using au adhesive, according to some embodiments of the subject technology.
Figure 4C:
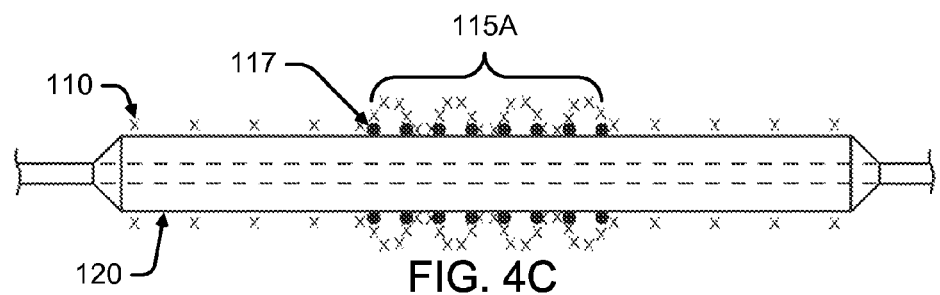
FIG. 4C depicts a vascular device coupled to an expanding member using an adhesive, according to some embodiments of the subject technology.

Referring to FIG. 4A, in one example, the adhesive 117 may be disposed between the expanding member 120 and a region 115A. The adhesive 117 adheres a portion of the region 115A to the outer surface of the expanding member 120. The adhesive 117 may be applied on the expanding member 120 and/or the vascular device 110, such that it only adheres a proximal and/or distal portion of the region 115A. Referring to FIG. 4C, alternatively, the adhesive 117 may be applied either throughout or at a particular portion of the region 115A. Referring to FIG. 4B, the adhesive 117 may be applied continuously or intermittently on the outer surface of the expanding member 120 or the vascular device 110, depending on the dissolvability and/or fracturability of the adhesive 117. The adhesive 117 may be applied by spray, dip, or other processes.

Figure 4D:
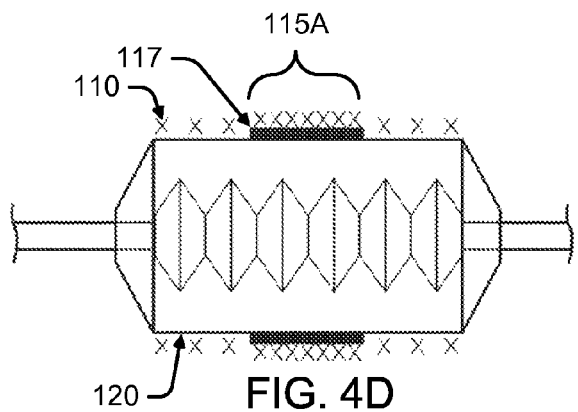
FIG. 4D depicts a vascular device coupled to an expanded expanding member using an adhesive, according to some embodiments of the subject technology.

Referring to FIG. 4D, in one aspect, the adhesive 117 may be applied on the outer surface of the expanding member 120 while the expanding member 120 is uniformly stretched, inflated, partially expanded, and/or in the expanded configuration. For example, the adhesive 117 may be applied on the outer surface of the expanding member 120 when the expanding member 120 is in the expanded configuration and uniformly stretched along its length. In this example, the adhesive 117 may be applied intermittently within the region 115A, such that unadhered areas are formed, as shown in FIG. 4C. The unadhered areas facilitate folding or collapsing of the expanding member 120 and vascular device 110 as the expanding member 120 and vascular device are prepared for deployment within the vasculature and moved to the collapsed configuration.

Alternatively, the adhesive 117 may be applied on the outer surface of the expanding member 120 while the expanding member 120 is deflated, partially collapsed, and/or in the collapsed configuration. In this example, the adhesive 117 may be applied continuously within the region 115A, as shown in FIG. 4B.

In another example, the adhesive 117 may be applied on the outer surface of the expanding member 120 while the expanding member 120 has a portion that is stretched along its length. The stretched portion may correspond to the region 115A of the vascular device 110.

In some aspects, the expanding member 120 and the vascular device 110 are positively engaged, coupled, attached, or adhered such that there is no shear strain in the adhesive 117 when the expanding member 120 and the vascular device 110 are in the expanded configuration. In other aspects, the expanding member 120 and the vascular device 110 are positively engaged, coupled, attached, or adhered such that there is enough shear strain in the adhesive 117, when the expanding member 120 and the vascular device 110 are fully expanded or in the expanded configuration, to fracture or sever the adhesive 117 and thereby release the vascular device 110 from the expanding member 120. In other aspects, the expanding member 120 and the vascular device 110 are positively engaged, coupled, attached, or adhered such that there is enough shear strain in the adhesive 117 when the expanding member 120 and the vascular device 110 are partially expanded to fracture or sever the adhesive 117 and thereby release the vascular device 110 from the expanding member 120 prior to full expansion of the expanding member 120. The shear strain of interest could be axial strain, hoop strain, or a combination of both.

Prior to deployment, the expanding member 120 may be moved to the collapsed configuration, with the vascular device 110 disposed thereon. When in the collapsed configuration, the region 115A of the body 111 will have a higher braid density and lower porosity than other portions of the body 111 due to the adhesive 117 bonding the region 115A to the expanding member 120. During subsequent expansion of the expanding member 120 and the vascular device 110, the overall porosity of the body 111 will decrease as the diameter of the vascular device 110 increases and the axial length of the vascular device 110 shortens. The porosity of the region 115A, however, also decreases and remains less porous than other portions of the body 111 during and after expansion.

Figure 5A:
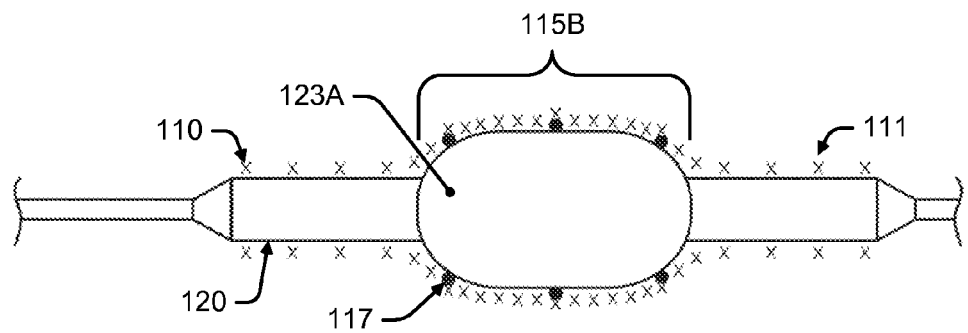
FIG. 5A depicts an expanding member having an enlarged region, according to some embodiments of the subject technology.
Figure 5B:
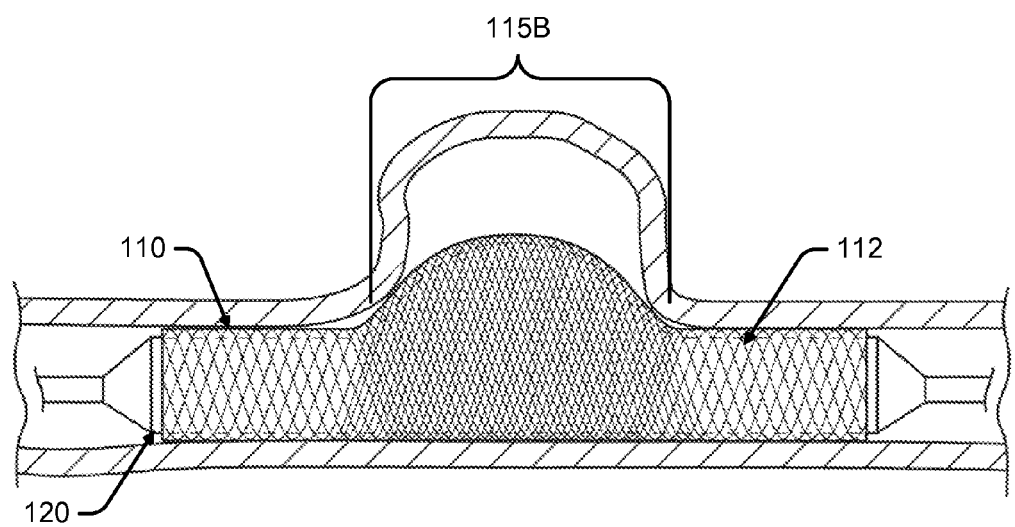
FIG. 5B depicts an expanding member having an enlarged region disposed within a vessel, according to some embodiments of the subject technology.

Referring to FIGS. 5A-5B, the expanding member 120 may controllably expand the vascular device 110 and attain the predetermined porosity for the region 115B by increasing a diameter of the region 115B of the vascular device 110 to a diameter that is larger than other portions of the vascular device 110. The expanding member 120 may comprise, when expanded, an enlarged region 123A having an enlarged diameter relative to other regions of the expanding member 120. The enlarged region 123A is substantially axially aligned with the region 115B.

The enlarged region 123A of the expanding member 120 increases the diameter of the region 115B to a diameter that is larger than the diameter in other portions of the body 111. Enlarging the diameter of the region 115B causes the members 112 disposed on the other portions of the body 111 to be pulled toward the region 115B, thereby decreasing the porosity within the region 115B. Accordingly, the expanding member 120 causes a reduction in the porosity of the body 111 within the region 115B that is more than the reduction of the porosity of the body 111 outside the region 115B, to thereby attain the predetermined porosity for the region 115B.

In one aspect, the adhesive 117 may be used to positively engage, couple, attach, or adhere the region 115B of the vascular device 110 to the enlarged region 123A of the expanding member 120. The adhesive 117 assists in utilizing the axial shrinkage and radial expansion characteristics of the expanding member 120 to control the porosity of the vascular device 110 by positively engaging, coupling, attaching, or adhering the expanding member 120 to the vascular device 110. The adhesion between the region 115B of the vascular device 110 and the expanding member 120 ensures that upon deployment, the region 115B attains the predetermined porosity.

Once near the treatment site, the adhesive 117 would begin to dissolve. As the expanding member 120 is expanded, the remaining adhesive 117 will be fractured, thereby further facilitating dissolution of the adhesive 117. The expanding member 120 and the vascular device 110 would expand in the same manner, shortening in axial length while increasing in diameter. The enlarged region 123A of the expanding member 120 would expand to a diameter greater than other portions of the expanding member 120, thereby causing the density within the region 115B to increase and the porosity within the region 115B to decrease, more than the other portions of the body 111.

Figure 6A:
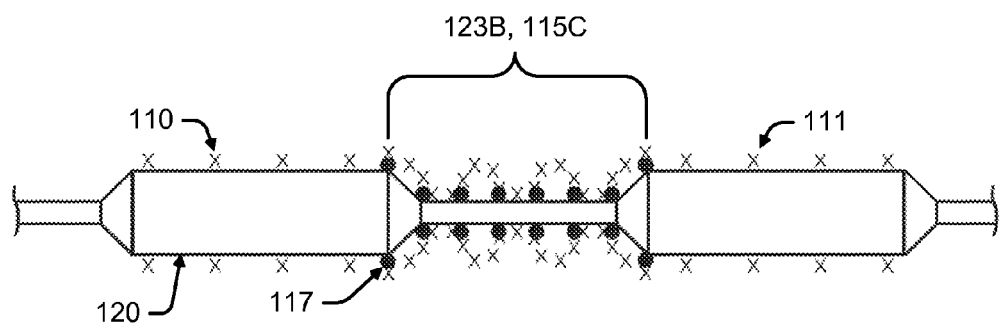
FIG. 6A depicts an expanding member having a reduced region, according to some embodiments of the subject technology.
Figure 6B:
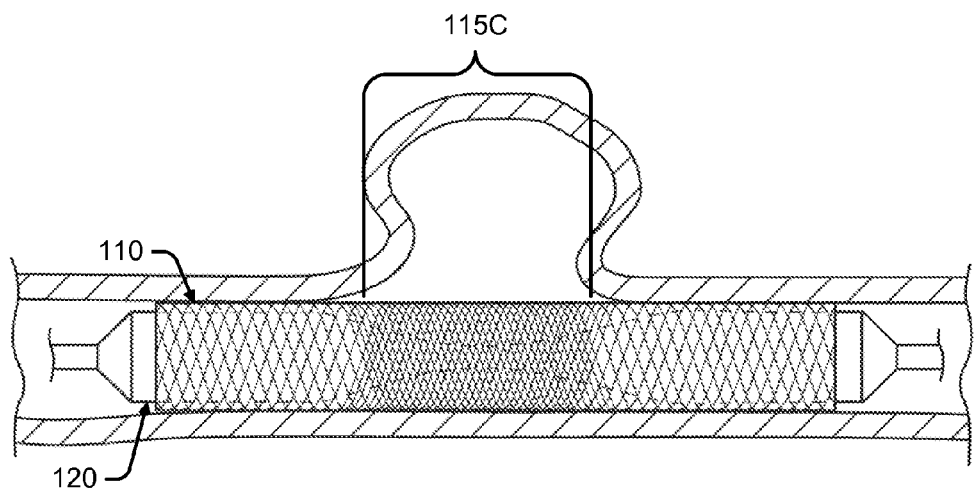
FIG. 6B depicts an expanding member having a reduced region disposed within a vessel, according to some embodiments of the subject technology.

Referring to FIGS. 6A-6B, the expanding member 120 may controllably expand the vascular device 110 and attain the predetermined porosity for the region 115O by storing excess material of the region 115O of the vascular device 110 within a reduced region 123B of the expanding member 120. For example, the expanding member 120 may comprise, when expanded, the reduced region 123B having a reduced diameter relative to other regions of the expanding member 120. The reduced region 123B is substantially axially aligned with the region 115O arid provides an area to store the excess material of the region 115C. In other words, the vascular device 110 may be arranged over the expanding member 120 so that the material of the region 115O may be bunched up and collected, in a highly dense arrangement, within the reduced region 123B of the expanding member 120.

In one aspect, the adhesive 117 may be used to adhere the proximal and/or distal portions of the body 111, with the region 115C unadhered, to the expanding member 120. In another example, the adhesive 117 may be disposed intermittently along the reduced region 123B, as shown in FIG. 6A. The adhesive 117 assists in maintaining the excess material of the region 115C within the reduced region 123B of the expanding member 120 so that upon deployment, the region 115O attains the predetermined porosity. Thus, upon expansion of the expanding member 120, the excess material of the region 115C stored at the reduced region 123B of the expanding member 120 will be deployed with comparatively reduced porosity.

Once near the treatment site, the adhesive 117 would begin to dissolve. As the expanding member 120 is expanded, the remaining adhesive 117 will be fractured, thereby further facilitating dissolution of the adhesive 117. The expanding member 120 and the vascular device 110 would expand in the same manner, shortening in axial length while increasing in diameter. The reduced region 123B of the expanding member 120, which houses the excess material of the region 115C, will begin to enlarge and deploy the excess material contained therein.

Figure 7A:
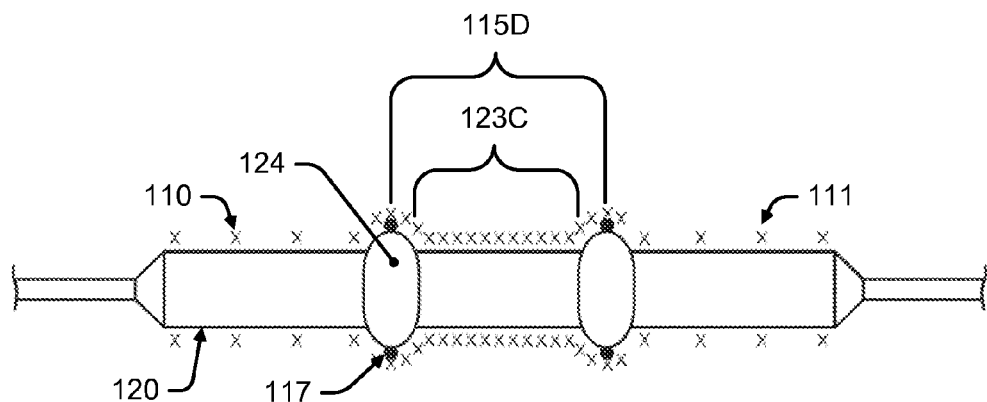
FIG. 7A depicts an expanding member having two enlarged regions, according to some embodiments of the subject technology.
Figure 7B:
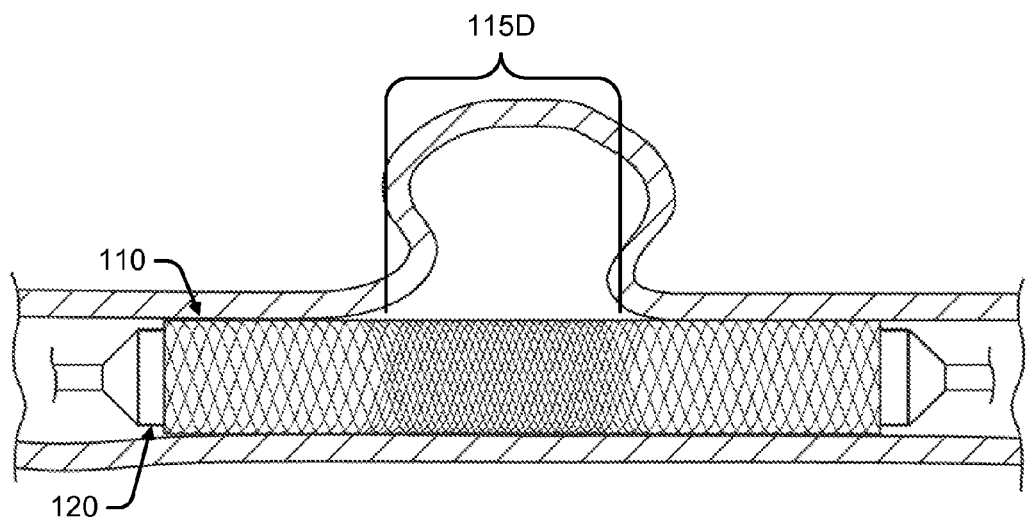
FIG. 7B depicts an expanding member having two enlarged regions disposed within a vessel, according to some embodiments of the subject technology.

Referring to FIGS. 7A-7B, the expanding member 120 may controllably expand the vascular device 110 and attain the predetermined porosity for the region 115D by storing excess material of the region 115D of the vascular device 110 within a region 123C disposed between two enlarged regions 124 of the expanding member 120. For example, the expanding member 120 may comprise, when expanded, two enlarged regions 124 having an enlarged diameter relative to a reduced region 123C therebetween. The reduced region 123C has a reduced diameter, is substantially axially aligned with the region 115D, and provides an area to store the excess material of the region 115D. In other words, the vascular device 110 may be arranged over the expanding member 120 so that the material of the region 115D may be bunched up and collected, in a highly dense arrangement, within the reduced region 123C of the expanding member 120.

In one aspect, the adhesive 117 may be used to adhere the proximal and/or distal portions of the body 111, with the region 115D unadhered, to the enlarged regions 124 of the expanding member 120. The adhesive 117 assists in maintaining the excess material of the region 115D within the reduced region 123C of the expanding member 120 so that upon deployment, the region 115D attains the predetermined porosity. Thus, upon expansion of the expanding member 120, the excess material of the region 115D stored at the reduced region 123C of the expanding member 120 will be deployed with comparatively reduced porosity.

Once near the treatment site, the adhesive 117 would begin to dissolve. As the expanding member 120 is expanded, the remaining adhesive 117 will be fractured, thereby further facilitating dissolution of the adhesive 117. The expanding member 120 and the vascular device 110 would expand in the same manner, shortening in axial length while increasing in diameter. The reduced region 123C of the expanding member 120, which houses the excess material of the region 115D, will begin to enlarge and deploy the excess material contained therein.

Radiopaque markers may be located adjacent the proximal or distal portions of the vascular device 110, and may be located at any position along the length of the vascular device 110 between a proximal and distal end of the vascular device 110, including the region 115A-D. The markers may be attached to the vascular device 110 by techniques such as adhesives, heat fusion, interference fit, fasteners, intermediate members, coatings, or by other techniques.

In some embodiments, the markers are comprised of ultrasonic markers, MRI-safe markers, or other markers. In some embodiments ultrasonic markers permit a physician to accurately determine the position of the vascular device 110 within a patient under ultrasonic visualization. Materials for an ultrasonic marker have an acoustical density sufficiently different from the vascular device 110 to provide suitable visualization via ultrasonic techniques. Exemplary materials comprise polymers, metals such as tantalum, platinum, gold, tungsten and alloys of such metals, hollow glass spheres or microspheres, and other materials.

In some embodiments, MRI-safe markers permit a physician to accurately determine the position of the vascular device 110 within a patient under magnetic resonance imaging. Exemplary materials for making MRI-safe marker have a magnetic signature sufficiently different from the vascular device 110 to provide suitable visualization via MRI techniques. Exemplary materials comprise polymers, metals such as tantalum, platinum, gold, tungsten and alloys of such metals, non-ferrous materials, and other materials.

A technique for treating an aneurysm will now be discussed with reference to FIGS. 8A-14. The vascular device 110 may be delivered into a treatment site using the system 100. The system 100 includes the catheter 130, which may for example, be an over the wire (OTW) catheter, a rapid exchange (multiple lumen) catheter, or a fixed wire catheter.

Figure 8A:
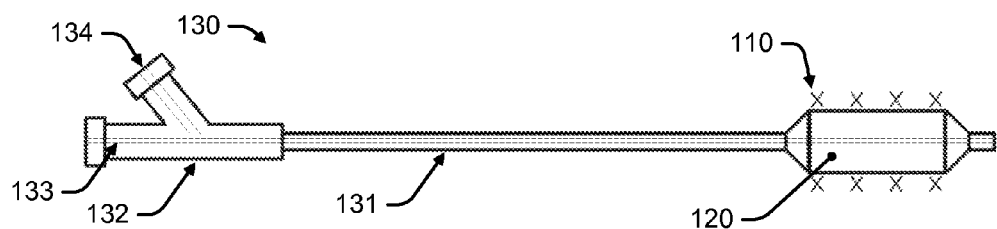
FIG. 8A depicts an example of a catheter, according to some embodiments of the subject technology.

Referring to FIG. 8A, the OTW catheter includes a shaft 131. A proximal portion of the shaft 131 has a manifold 132 affixed thereto. A distal portion of the shaft 131 has the expanding member 120 affixed thereto. The shaft 131 also includes two lumens, a guide wire lumen 133 and an inflation lumen 134 for expanding or inflating the expanding member 120. A proximal end of each lumen 133, 134 is configured to interface with the manifold 132.

Figure 8B:
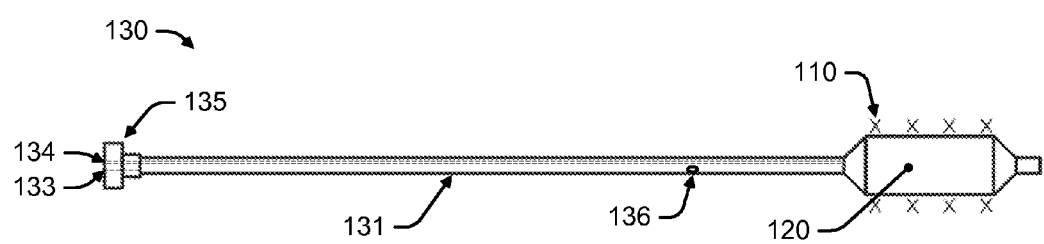
FIG. 8B depicts another example of a catheter, according to some embodiments of the subject technology.

Referring to FIG. 8B, the rapid exchange catheter includes a shaft 131 having an inflation lumen 134 extending therethrough. A proximal portion of the shaft 131 has a hub 135 affixed thereto. A distal portion of the shaft 131 has the expanding member 120 affixed thereto. The shaft 131 has two lumens over a distal portion only. The inflation lumen 134 and a guide wire lumen 133 which extends from a distal end of the shaft 131, to a skive 136. At the skive 136, the guide wire lumen 133 terminates and a guide wire communicates with an outer surface of the shaft 131. The inflation lumen 134 is configured to expand or inflate the expanding member 120.

The fixed wire catheter includes a shaft having an inflation lumen only, to which is affixed a hub and the expanding member 120.

Figure 9:
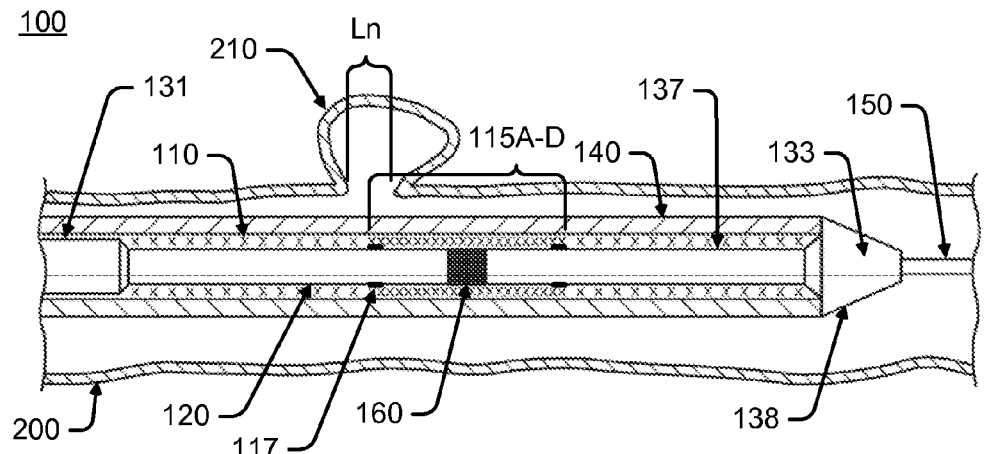
FIG. 9 depicts a cross section view of a vessel and delivery of a vascular device according to some embodiments of the subject technology.

Referring to FIG. 9, prior to delivery, the vascular device 110 is mounted to the expanding member 120 either with or without adhesive 117. An outer sheath 140 is disposed over the vascular device 110 and the expanding member 120 to confine, within an annular space between the outer sheath 140 and the expanding member 120, the vascular device 110 in the first, collapsed configuration. The outer sheath 140 also retains the vascular device 110 and the expanding member 120 in an axial elongated and diametrically reduced configuration.

The vascular device 110 and the expanding member 120 may be cooperatively movable within the outer sheath 140 in order to deliver the vascular device 110 to a treatment site, such as an aneurysm, within the vasculature of a patient.

The outer sheath 140 may be configured to be introduced and advanced through the vasculature of the patient. The outer sheath 140 may be made from various thermoplastics, e.g., PTFE, FEP, HDPE, PEEK, etc., which may optionally be lined on the inner surface of the outer sheath 140 or an adjacent surface with a hydrophilic material such as PVP or some other plastic coating. Additionally, either surface may be coated with various combinations of different materials, depending upon the desired results.

The shaft 131 includes the guide wire lumen 133 for allowing a guide wire 150 to extend therethrough. The shaft 131 may also include a reduced diameter at a distal region 137 to provide sufficient annular space in which the vascular device 110 is stowed. In this example, the expanding member 120 would be disposed on the reduced diameter region 137 of the shaft 131.

Radiopaque markers may be provided at various locations along the length of the system 100. For example, an enlarged distal tip 138 of the shaft 131 may be radiopaque. In another example, radiopaque markers may be provided on the reduced diameter distal region 137 of the shaft, beneath the distal and proximal end of the vascular device 110. In yet another example, a radiopaque marker 160 may be disposed on the shaft 131 adjacent to a longitudinal center of the vascular device 110 and/or the expanding member 120.

In one aspect, the vascular devices 110 may be configured with regions 115A-D having different axial lengths. A physician may select the appropriate vascular device 110 based on a size of the neck of the aneurysm and the axial length of the region 115A-D. For example, based on the axial length of the region 115A-D and a length of a neck of the aneurysm "Ln," the vascular device 110 may be selected such that the axial length of the region 115A-D, when the vascular device 110 is in the second, expanded configuration, is longer than the length of the neck of the aneurysm.

In another aspect, the system 100 may be manufactured to ship with the expanding member 120 and the vascular device 110 in the expanded configuration. In this example, after the system 100 is selected such that the as-delivered axial length of the region 115A-D is longer than the length of the aneurysm, the physician may draw the vascular device 110 and the expanding member 120 assembly proximally into the outer sheath 140 to compress the vascular device and the expanding member 120 assembly. In an alternative embodiment, the system 100 may be manufactured to ship with the expanding member 120 and the vascular device 110 in the collapsed configuration, preloaded in the outer sheath 140.

Referring to FIG. 9, the system 100 is advanced percutaneously over the guide wire 150 to the treatment site, in this example to the site of an aneurysm 210. Specifically, the vascular device 110 may be positioned in a vessel 200 at an ostium or the neck of the aneurysm 210. In one aspect, the radiopaque marker 160 may be positioned distal to a distal lateral wall of the aneurysm 210, thereby offsetting the region 115A-D from the ostium of the aneurysm 210 prior to expanding the vascular device 110. During delivery, any dissolvable adhesive 117 disposed between the vascular device 110 and the expanding member 120 is protected from dissolving by the outer sheath 140. Specifically, the outer sheath 140 covers the vascular device 110 and the expanding member 120 assembly and thereby prevents any fluids, such as blood, from coming into contact with the adhesive 117.

Figure 10:
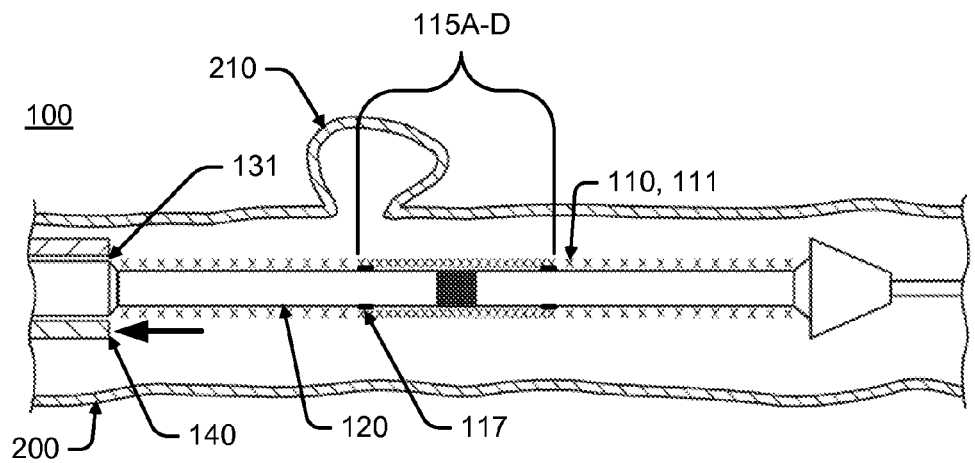
FIG. 10 depicts a cross section view of a vessel and delivery of a vascular device according to some embodiments of the subject technology.

Referring to FIG. 10, after navigating the system 100 to the treatment site within the patient, the outer sheath 140 is withdrawn proximally while maintaining the position of the shaft 131 to thereby expose a distal portion of the shaft 131, the expanding member 120, and the vascular device 110. The outer sheath 140 is withdrawn until a distal end of the outer sheath 140 is proximal of the vascular device 110 and the expanding member 120 assembly.

If the vascular device 110 comprises a self-expanding stent, then portions of the vascular device that may be unadhered to the expanding member 120 may partially diametrically expand and partially axially shorten. In this example the region 115A-D will maintain a higher density and lower porosity than other portions of the body 111, during and after deployment, because of the adhesive 117 disposed between the region 115A-D and the expanding member 120. The adhesive 117 thereby allows the expandable member 120 to controllably expand the vascular device 110 and attain the predetermined porosity for the region 115A-D by positively engaging the vascular device 110. Alternatively, if the vascular device 110 does not comprise a self-expanding stent, then the vascular device 110 remains on the expanding member 120. As the outer sheath 140 is withdrawn, thereby exposing the vascular device 110 and the expanding member 120 assembly, the adhesive 117 begins to make contact with fluids, such as blood. The adhesive 117 begins to dissolve due to the contact with the fluid.

Figure 11:
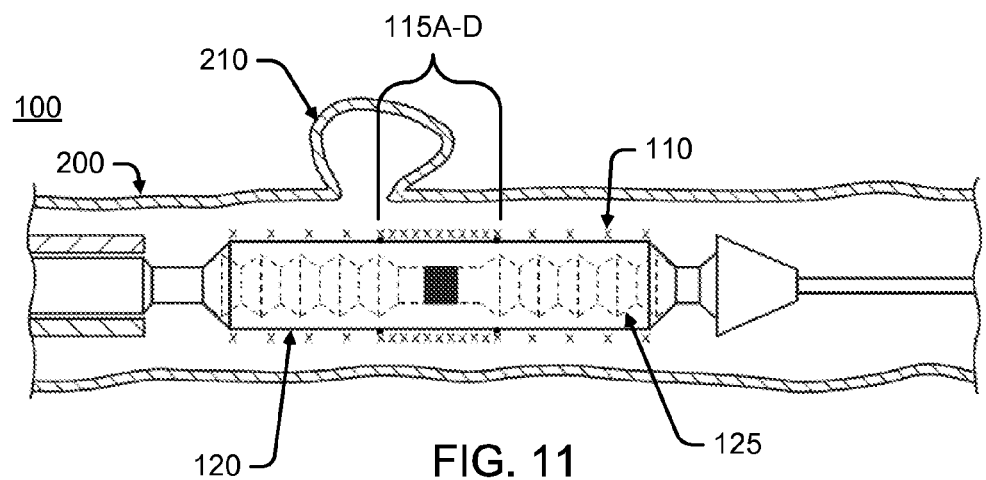
FIG. 11 depicts a cross section view of a vessel and delivery of a vascular device according to some embodiments of the subject technology.
Figure 12:
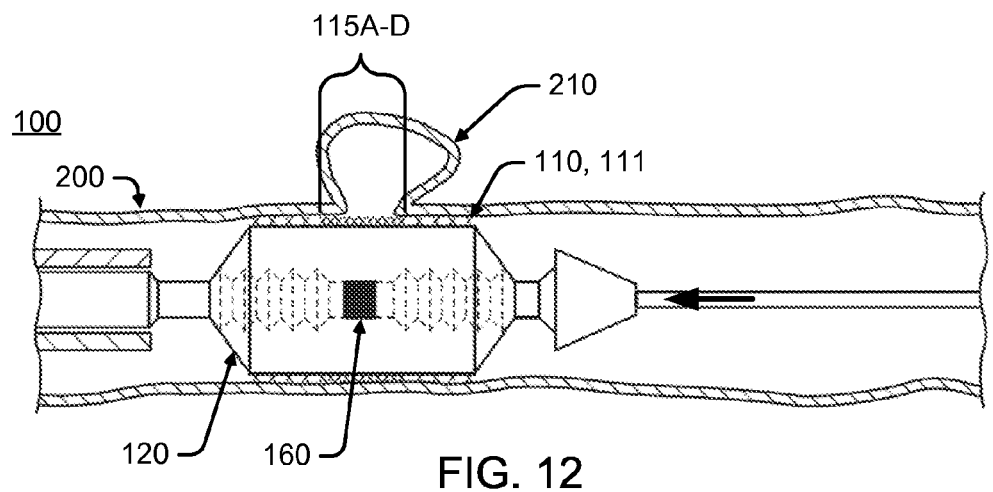
FIG. 12 depicts a cross section view of a vessel and delivery of a vascular device according to some embodiments of the subject technology.

Referring to FIG. 11, as the expanding member 120 is partially expanded or inflated using the inflation lumen 134, the expanding member 120 and hence, the vascular device 110, partially diametrically expand and partially axially shorten. During expansion of the expanding member 120, the inner member 125 also axially shortens by the same amount as the expanding member 120 and/or the vascular device 110, Referring to FIG. 12, the system 100 is then withdrawn proximally, until the radiopaque marker 160 is centered along the length of the ostium or neck of the aneurysm 210. In other words, after the vascular device 110 has been repositioned such that the region 115A-D is centered along the length of the ostium, the region 115A-D will cover the ostium or neck of the aneurysm 210 when the vascular device 110 is in the second, expanded configuration.

The expanding member 120 is then expanded to the fully expanded configuration, thereby fully deploying the vascular device 110. The expanding member 120 will diametrically expand and axially shrink, while maintaining the vascular device 110 to its outer surface due to the remaining adhesive 117 disposed between the vascular device 110 and the expanding member. The expanding member 120 controllably expands the vascular device 110 such that the vascular device 110 attains the predetermined porosity at the region 115A-D. During deployment, the expanding member 120 causes a reduction in the porosity of the body 111 within the region 115A-D that is more than the reduction of the porosity of the body 111 outside the region 115A-D, thereby attaining the predetermined porosity for the region 115A-D.

The adhesive 117 disposed between the expanding member 120 and the vascular device 110 may dissolve and/or fracture during or after expansion of the expanding member 120, thereby releasing the vascular device 110 from the expanding member 120.

The expanding member 120 thereby causes the region 115A-D to attain the pre-programmed porosity regardless of the endless variety of physician induced movements that can occur during the deployment of the vascular device 110. Stated another way, the porosity of the region 115A-D is relatively insensitive to physician applied motions during deployment of the vascular device 110.

Figure 13:
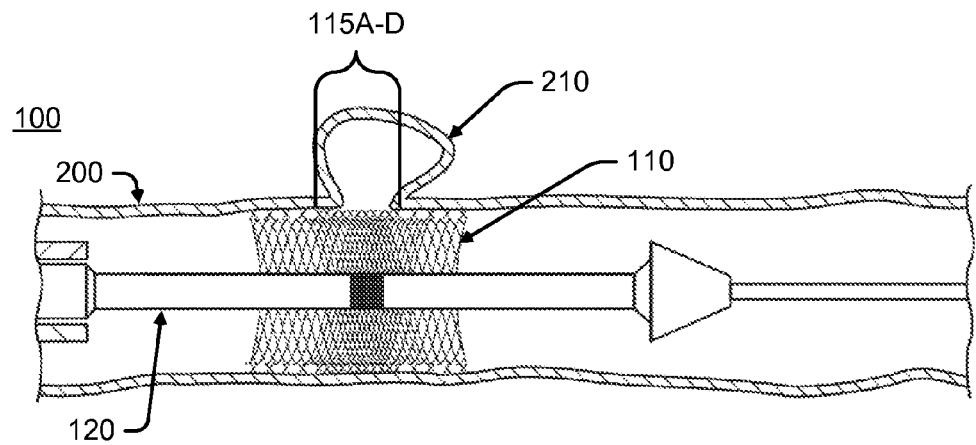
FIG. 13 depicts a cross section view of a vessel and delivery of a vascular device according to some embodiments of the subject technology.
Figure 14:
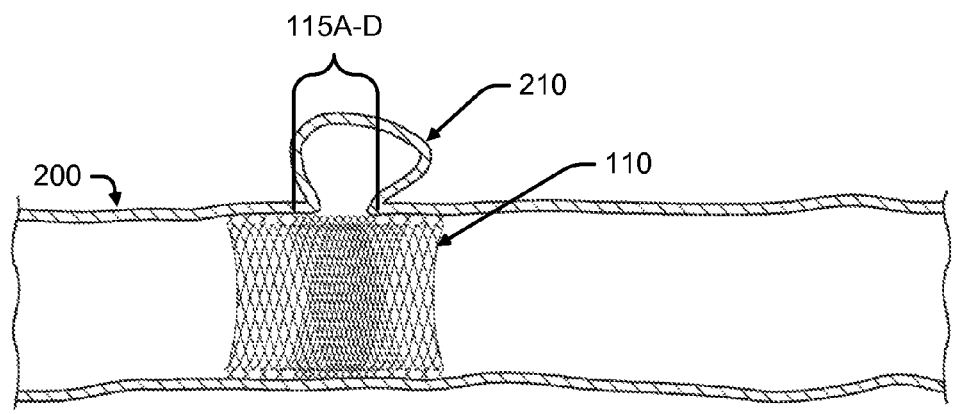
FIG. 14 depicts a cross section view of a vessel and a vascular device according to some embodiments of the subject technology.

Referring to FIG. 13, once the entire vascular device 110 is fully expanded, the expanding member 120 is collapsed or deflated. Referring to FIG. 14, thereafter, the catheter 130, along with the outer sheath 140, shaft 131, expanding member 120, and guide wire 150 may be withdrawn from the body.

The region 115A-D or the vascular device 100 has a significantly lower porosity compared to other portions of the body 111. Due to the lower porosity of the region 115A-D, less blood flows into the aneurysm 210 such that substantial thrombosis may occur within the aneurysm 210.

In one arrangement, the vascular device 110 may be comprised of metal, polymer, ceramic, permanent enduring materials, and may comprise either of or both of non-bioabsorbable and bioabsorbable materials. Exemplary materials include, but are not limited to, NITINOL®, stainless steel, cobalt chromium alloys, Elgiloy, magnesium alloys, polylactic acid, poly glycolic acid, poly ester amide (PEA), poly ester urethane (PEU), amino acid based bioanalogous polymers, tungsten, tantalum, platinum, polymers, bio-polymers, ceramics, bio-ceramics, or metallic glasses. Part or all of the medical device may elute over time substances such as drugs, biologics, gene therapies, antithrombotics, coagulants, anti-inflammatory drugs, immunomodulator drugs, anti-proliferatives, migration inhibitors, extracellular matrix modulators, healing promoters, re-endothelialization promoters, or other materials. In some embodiments, the vascular device 110 may be formed from materials having shape memory properties. In some embodiments, the vascular device 110 may be finished by processes to remove slag. In some embodiments, the vascular device 110 may be subjected to a tempering treatment at temperatures customarily applied to the material so that the impressed structure is permanently established.

The vascular device 110 may have various lengths and diameters. For example, the vascular device 110 may have specific cross-sectional diameters, the diameters being measured when the vascular device 110 is fully free to expand, ranging from about 2 mm to about 6 mm. If the vascular device 110 has a diameter between 3 mm and 4 mm, it may be used in a size 18 microcatheters (i.e., microcatheters with an inner diameter of approximately 0.21 inch). If the vascular device 110 has a diameter between 5 mm and 6 mm, it may be used in a size 27 microcatheters (i.e., microcatheters with an inner diameter of approximately 0.027 inch). However, other suitable cross-sectional diameters may be used without deviating from the scope of the subject technology. In some embodiments, the vascular device 110 may have lengths, measured proximally to distally along the longitudinal axis of the vascular device 110, ranging from 15 mm to 40 mm, though other ranges and sizes are also possible.

Skilled artisans may implement the described functionality in varying ways for each particular application. Various components and blocks may be arranged differently (for example, arranged in a different order, or partitioned in a different way) all without departing from the scope of the subject technology. It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (for example, his) include the feminine and neuter gender (for example, her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "aspect" does not imply that such aspect is essential to the subject technology or that such aspect applies to all configurations of the subject technology. A disclosure relating to an aspect may apply to all aspects, or one or more aspects. An aspect may provide one or more examples. A phrase such as an "aspect" may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manlier similar to the term "comprise" as "comprise" is interpreted when employed as a transitional word in a claim.

What is claimed is:

1. A method for manufacturing a vascular device, comprising:
    disposing a vascular device over an expanding member, the vascular device comprising a body having a substantially uniform porosity that is adapted to change by adjusting an axial length of the body; and
    adhering a portion of the body to the expanding member such that upon radial expansion of the expanding member, adherence between the body portion and the expanding member reduces a porosity of the body within the body portion more than the expanding member reduces a porosity of the body outside the body portion by axially shortening the body portion with the expanding member.

2. The method of claim 1, wherein the adhering occurs when the expanding member is in an expanded configuration.

3. The method of claim 2, wherein the expanding member in the expanded configuration is uniformly stretched when unrestrained.

4. The method of claim 1, wherein the adhering occurs when the expanding member is in a collapsed configuration.

5. The method of claim 1, wherein the adherence between the body portion and the expanding member is configured to sever upon at least partial expansion of the expanding member.

6. The method of claim 1, wherein the adherence between the body portion and the expanding member is configured to sever when the expanding member is expanded to more than 80% the expanding member's fully expanded configuration.

7. The method of claim 1, wherein the adherence between the body portion and the expanding member is configured to sever due to shear strain in the adherence upon expansion of the expanding member.

8. A method for manufacturing a vascular device, comprising:
    aligning a region of a vascular device with an area of an expanding member, the vascular device having a substantially uniform porosity that is altered by adjustment of an axial length of the vascular device; and
    adhering the region of the vascular device to the area of the expanding member such that upon radial expansion of the expanding member, adherence between the vascular device and the expanding member reduces a porosity of the region more than the adherence reduces a porosity outside the region by axially shortening the region with the expanding member.

9. The method of claim 8, wherein the adhering occurs when the expanding member is in a radially expanded configuration.

10. The method of claim 8, wherein the adhering occurs when the expanding member is in a collapsed configuration.

11. The method of claim 8, wherein the adherence between the region of the vascular device and the area of the expanding member is configured to sever upon at least partial expansion of the expanding member.

12. The method of claim 8, wherein the adherence between the region of the vascular device and the area of the expanding member is configured to sever when the expanding member is expanded to more than 80% the expanding member's fully expanded configuration.

13. The method of claim 8, wherein the adherence between the region of the vascular device and the area of the expanding member is configured to sever due to shear strain in the adherence upon expansion of the expanding member.

14. A method for treating an aneurysm, the method comprising:
    positioning a vascular device in a vessel at an ostium of the aneurysm, the vascular device comprising a body having a substantially uniform porosity that is adapted to change by adjusting an axial length of the body;
    inflating an expanding member positioned within a central lumen of the body; and
    reducing a porosity of the body within a body region more than a porosity of the body is reduced outside the body region as the body is radially expanded, by engaging the body with the expanding member and axially shortening the body region with the expanding member.

15. The method of claim 14, wherein the positioning comprises axially offsetting the body region from the ostium of the aneurysm prior to expanding the vascular device.

16. The method of claim 14, further comprising reducing an axial length of the expanding member by axially collapsing a corrugated tube positioned within the expanding member.

17. The method of claim 14, further comprising dissolving an adhesive that bonds a portion of the body to the expanding member.

18. The method of claim 14, further comprising expanding the body, wherein the body comprises a self-expanding braided structure or cut metal tube.

19. The method of claim 14, wherein an axial length of the expanding member in a collapsed configuration is about 200-500% longer than the axial length of the expanding member in a radially expanded configuration.

20. The method of claim 19, wherein a change in the axial length of the expanding member from the collapsed configuration to the expanded configuration is the same as a change in the axial length of the body from a body collapsed configuration to a body expanded configuration.

21. A method for treating an aneurysm, the method comprising:
    positioning a vascular device in a vessel at an ostium of the aneurysm, the vascular device having a porosity that is altered by adjustment of an axial length of the vascular device;
    expanding an expanding member positioned within a lumen of the vascular device; and
    reducing a porosity of the vascular device within a region more than a porosity of the vascular device is reduced outside the region by axially shortening the region with the expanding member.

22. The method of claim 21, wherein the positioning comprises axially offsetting the region from the ostium of the aneurysm prior to expanding the expanding member.

23. The method of claim 21, further comprising reducing an axial length of the expanding member by axially collapsing a corrugated tube positioned within the expanding member.

24. The method of claim 21, further comprising dissolving an adhesive that bonds a portion of the vascular device to a portion of the expanding member.

25. The method of claim 21, wherein an axial length of the expanding member in a collapsed configuration is about 200-500% longer than the axial length of the expanding member in an expanded configuration.

26. The method of claim 25, wherein a change in the axial length of the expanding member from the collapsed configuration to the expanded configuration is the same as a change in the axial length of the vascular device from a device collapsed configuration to a device expanded configuration.

* * * * *